United States Patent
Imai

(10) Patent No.: US 11,439,368 B2
(45) Date of Patent: Sep. 13, 2022

(54) ACOUSTIC WAVE PROCESSING DEVICE, SIGNAL PROCESSING METHOD FOR ACOUSTIC WAVE PROCESSING DEVICE, AND PROGRAM

(71) Applicant: FUJIFILM Corporation, Tokyo (JP)

(72) Inventor: Yoshiro Imai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 392 days.

(21) Appl. No.: 15/227,085

(22) Filed: Aug. 3, 2016

(65) Prior Publication Data

US 2016/0338673 A1 Nov. 24, 2016

Related U.S. Application Data

(63) Continuation of application No. PCT/JP2014/076283, filed on Oct. 1, 2014.

(30) Foreign Application Priority Data

Mar. 24, 2014 (JP) ............................ JP2014-060158

(51) Int. Cl.
*G01S 7/52* (2006.01)
*A61B 8/06* (2006.01)
(Continued)

(52) U.S. Cl.
CPC .............. *A61B 8/5207* (2013.01); *A61B 8/06* (2013.01); *A61B 8/14* (2013.01); *A61B 8/469* (2013.01);
(Continued)

(58) Field of Classification Search
CPC ........... A61B 8/08; A61B 8/14; A61B 8/5246; A61B 8/06; A61B 8/5207; A61B 8/488;
(Continued)

(56) References Cited

U.S. PATENT DOCUMENTS 4,790,322 A * 12/1988 Iinuma ..................... A61B 8/06
600/456
4,972,838 A * 11/1990 Yamazaki ............. B82Y 15/00
600/455
(Continued)

FOREIGN PATENT DOCUMENTS

JP 58-44372 A 3/1983
JP 2004-344257 * 9/2004 ............... A61B 8/06
(Continued)

OTHER PUBLICATIONS

Powers et al., "Medical Ultrasound Systems", Interface Focus (2011) 1, 477-489).*
(Continued)

*Primary Examiner* — Keith M Raymond
*Assistant Examiner* — Amy Shafqat
(74) *Attorney, Agent, or Firm* — Birch, Stewart, Kolasch & Birch, LLP

(57) ABSTRACT

The acoustic wave processing device includes a data processing unit which performs superimposition processing on first element data or first reception data generated by performing phasing addition on the first element data to generate processed data, an image generation unit which generates a B mode image based on the first element data and the processed data, a bloodstream image generation unit which generates a bloodstream image based on bloodstream information included in the first element data, a region setting unit which sets a bloodstream image region, a processing region setting unit which sets a region for processing in the data processing unit based on information relating to the bloodstream image region, and a display image generation unit which generates a synthesized image of the B mode image and the bloodstream image.

16 Claims, 14 Drawing Sheets

(51) Int. Cl.
  *A61B 8/08* (2006.01)
  *A61B 8/14* (2006.01)
  *A61B 8/00* (2006.01)
  *G01S 15/89* (2006.01)
  *G10K 11/34* (2006.01)

(52) U.S. Cl.
  CPC .......... *A61B 8/488* (2013.01); *G01S 7/52046* (2013.01); *G01S 7/52063* (2013.01); *G01S 15/8915* (2013.01); *G01S 15/8988* (2013.01); *G10K 11/346* (2013.01)

(58) Field of Classification Search
  CPC ..... A61B 8/469; A61B 8/5238; A61B 8/5269; G01S 7/52; G01S 15/8915; G01S 15/8988; G01S 7/52046; G01S 7/52063; G10K 11/346
  USPC .......................................................... 600/441
  See application file for complete search history.

(56) References Cited

U.S. PATENT DOCUMENTS

| | | | | |
|---|---|---|---|---|
| 2003/0013959 | A1* | 1/2003 | Grunwald | A61B 8/468 600/437 |
| 2010/0076313 | A1* | 3/2010 | Katsuyama | G01S 7/52036 600/443 |
| 2010/0331693 | A1* | 12/2010 | Matsunaga | A61B 8/4281 600/443 |
| 2011/0077522 | A1* | 3/2011 | Sato | G01S 15/8995 600/447 |
| 2011/0144498 | A1* | 6/2011 | Ando | A61B 8/466 600/443 |
| 2012/0123273 | A1* | 5/2012 | Okuno | A61B 8/12 600/459 |
| 2013/0006111 | A1* | 1/2013 | Sasaki | G01S 7/52074 600/441 |
| 2013/0245445 | A1* | 9/2013 | Kakee | A61B 8/54 600/440 |
| 2014/0140600 | A1* | 5/2014 | Daigle | G01S 7/52046 382/131 |
| 2014/0276072 | A1* | 9/2014 | Martins | A61B 8/488 600/454 |
| 2015/0112198 | A1* | 4/2015 | Yamamoto | G01S 7/52049 600/447 |
| 2015/0196274 | A1* | 7/2015 | Yamamoto | A61B 8/485 600/442 |
| 2015/0196283 | A1* | 7/2015 | Yamamoto | A61B 8/485 600/437 |
| 2015/0222838 | A1* | 8/2015 | Kawabata | A61B 8/06 348/77 |
| 2015/0250446 | A1* | 9/2015 | Kanayama | A61B 8/468 600/438 |
| 2015/0374339 | A1* | 12/2015 | Yamamoto | G01S 7/52046 600/447 |

FOREIGN PATENT DOCUMENTS

| | | | | |
|---|---|---|---|---|
| JP | 2004-344257 | A | 12/2004 | |
| JP | 2004344257 | | * 12/2004 | ............... A61B 8/00 |
| JP | 2004344257 | A | * 12/2004 | |
| JP | 2005-204761 | | * 4/2005 | ............... A61B 8/00 |
| JP | 2005-204761 | A | 8/2005 | |
| JP | 2005204761 | | * 8/2005 | ............... A61B 8/00 |
| JP | 2009-536853 | A | 10/2009 | |
| JP | 2012215721 | | * 9/2012 | ............... A61B 8/00 |
| JP | 2014-30715 | A | 2/2014 | |

OTHER PUBLICATIONS

JP 2005-204761 machine translation from AIPN Japan Patent Office.*
JP 2004-344257 machine translation from AIPN Japan Patent Office.*
English translation of the International Preliminary Report on Patentability and the Written Opinion of the International Searching Authority, dated Sep. 27, 2016, for International Application No. PCT/JP2014/076283.
Chinese Office Action and Search Report, dated Jul. 12, 2018, for Chinese Application No. 201480075630.3, with an English translation of the Office Action.
International Search Report, issued in PCT/JP2014/076283, PCT/ISA/210, dated Jan. 6, 2015.
Written Opinion of the International Searching Authority, issued in PCT/JP2014/076283, PCT/ISA/237, dated Jan. 6, 2015.

* cited by examiner

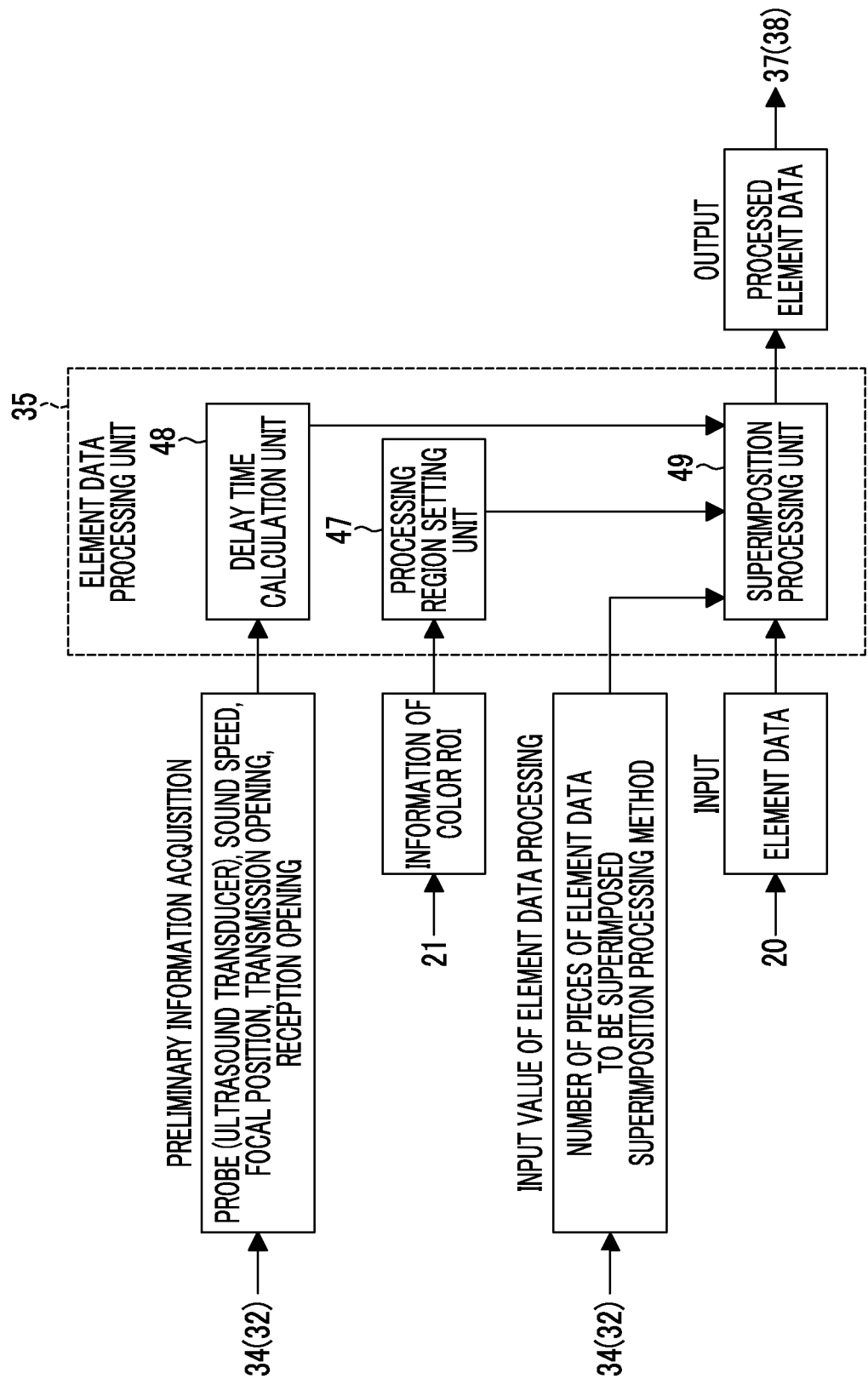

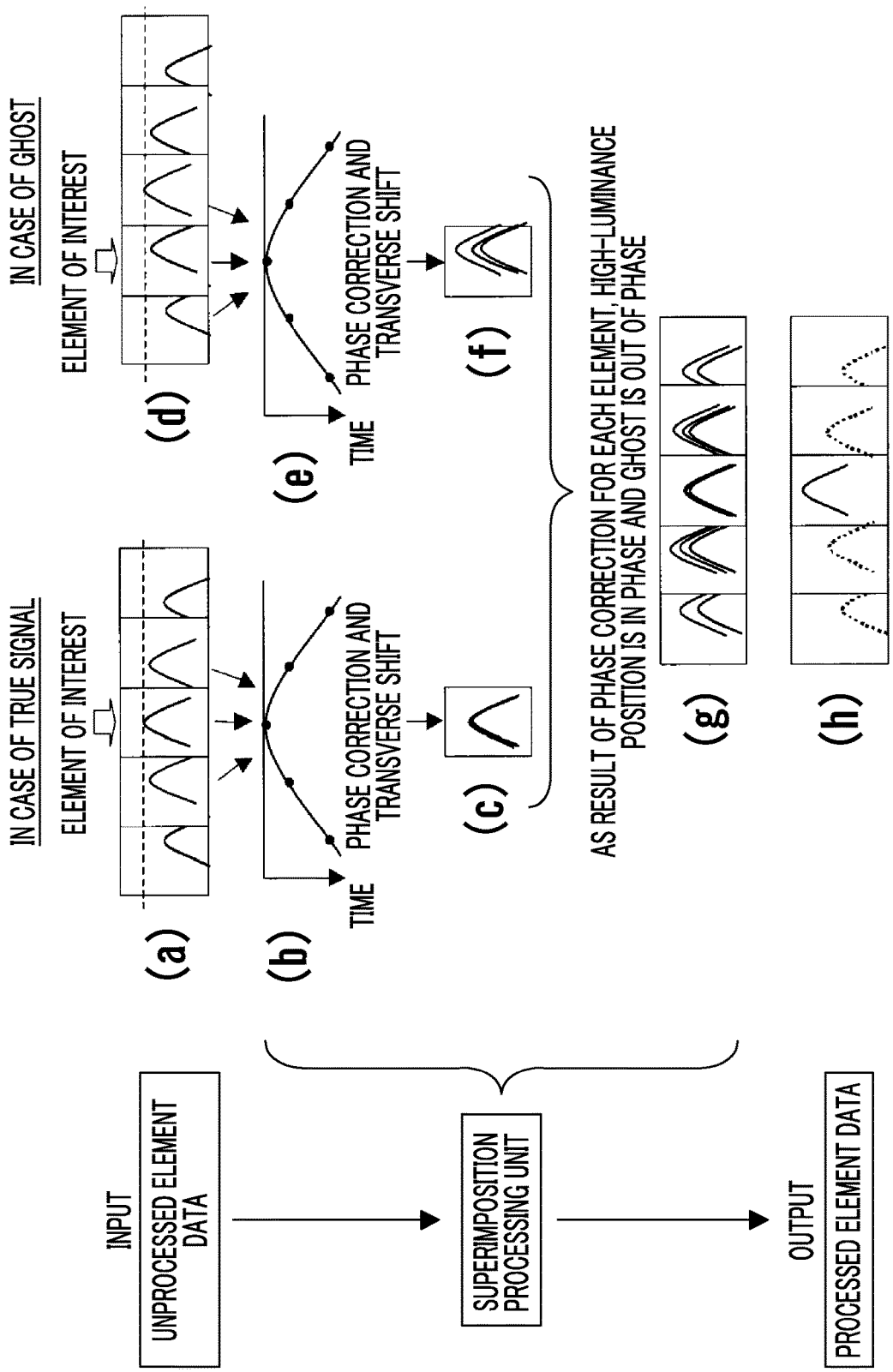

ACOUSTIC WAVE PROCESSING DEVICE, SIGNAL PROCESSING METHOD FOR ACOUSTIC WAVE PROCESSING DEVICE, AND PROGRAM

CROSS-REFERENCE TO RELATED APPLICATIONS

This application is a Continuation of PCT International Application No. PCT/JP2014/076283 filed on Oct. 1, 2014, which claims priority under 35 U.S.C § 119 (a) to Japanese Patent Application No. 2014-060158 filed on Mar. 24, 2014. Each of the above application(s) is hereby expressly incorporated by reference, in its entirety, into the present application.

BACKGROUND OF THE INVENTION

1. Field of the Invention

The present invention relates to an acoustic wave processing device, a signal processing method, and a non-transitory computer readable recording medium storing a program which transmit and receive an acoustic beam to capture an image of an inspection object, such as an organ in a living body, and generate an acoustic image or the like for inspection or diagnosis of the inspection object.

2. Description of the Related Art

Hitherto, an acoustic diagnostic apparatus, such as an ultrasound image diagnostic apparatus, which generates an ultrasound image for inspection or diagnosis of an inspection object using an acoustic wave, such as an ultrasonic wave has come into practical use in the medical field.

In general, this kind of ultrasound diagnostic apparatus has an ultrasound probe (hereinafter, referred to as a probe) in which a plurality of elements (ultrasound transducers) are embedded, and an apparatus body connected to the probe. In the ultrasound diagnostic apparatus, an ultrasound beam is transmitted from a plurality of elements of the probe toward a subject (inspection object) so as to form a predetermined focal point (transmission focal point), an ultrasonic echo from the subject is received by the probe, and the reception signal of the received ultrasonic echo is electrically processed by the apparatus body to generate an ultrasound image.

Examples of an ultrasound image which is acquired in the ultrasound diagnostic apparatus include a B mode image which is image information relating to a tissue of a subject based on the intensity of an ultrasonic wave reflected by the subject and a two-dimensional Doppler image which is information relating to the movement of a biological tissue (for example, blood) in the subject based on frequency shift information due to a Doppler effect included in the reflected ultrasonic wave.

The movement of the bloodstream is confirmed on a tomographic image of the subject in a display mode, called a color mode, in which a color Doppler image with blood colored according to the moving direction or the moving speed of blood and a B mode image are synthesized and a synthesized image is displayed.

On the other hand, the ultrasound beam drives a plurality of elements based on a predetermined transmission delay pattern and is transmitted so as to form the set focal point. This ultrasound beam has a shape having a width in a transverse direction. For this reason, there is a problem in that information of a reflection point at a position shifted in a transverse direction is picked up, and is reproduced on the ultrasound image as a so-called ghost signal.

In regard to this problem, the ultrasound diagnostic apparatus performs so-called multiline processing for superimposing a plurality of pieces of data (element data or reception data) obtained by each transmission according to the reception time or the position of each element to correct data in the generation of one ultrasound image (JP1983-044372A JP S58-44372-A) and JP2009-536853A). In a case of ghost signals, even if the pieces of data are superimposed according to the reception time or the position of each element, ghost signals are superimposed due to a shifted state and cancel each other; thus, it is possible to remove the ghost signals.

SUMMARY OF THE INVENTION

However, the multiline processing has a high calculation load, requires a lot of processing time, and causes degradation of a frame rate. In particular, a problem occurs in a case of a small diagnostic apparatus in which a high-performance arithmetic device cannot be mounted.

In the color mode, when generating a color Doppler image, typically, transmission is performed multiple times in the same direction in order to secure sensitivity when detecting a Doppler effect. That is, in order to secure sensitivity and to improve image quality, it is necessary to increase the number of transmissions in the same direction. For this reason, typically, the frame rate is degraded compared to the B mode.

For this reason, in the color mode in which the B mode image and the color Doppler image are displayed in a superimposed manner, if multiline processing is performed when generating the B mode image, the frame rate is significantly degraded, and real time performance is damaged.

The invention has been accomplished in order to solve the problems in the related art, and an object of the invention is to provide an acoustic wave processing device, a signal processing method, and a non-transitory computer readable recording medium storing a program capable of improving image quality while suppressing degradation of the frame rate and securing real time performance in a color mode, in which a B mode image and a color Doppler image are synthesized and displayed.

The inventors have intensively studied in order to attain the above-described object and have found that the above-described problems can be solved by providing a data processing unit which selects two or more of pieces of data from among a plurality of pieces of first element data or a plurality of pieces of first reception data generated by performing phasing addition processing on the first element data and performs superimposition processing on the selected two or more pieces of data to generate processed data, a B mode image generation unit which generates a B mode image based on at least one of the first element data or the processed data generated by the data processing unit, a bloodstream image generation unit which generates a bloodstream image based on bloodstream information included in the first element data, a region setting unit which sets a bloodstream image region where the bloodstream image generation unit generates the bloodstream image, a processing region setting unit which sets a processing region where the data processing unit performs processing based on information relating to the bloodstream image region set by the region setting unit, and a display image generation unit which generates a synthesized image of the B mode image and the bloodstream image based on the information relating to the bloodstream image region set by the region setting unit.

That is, the invention provides (1) to (11) described below.

(1) An acoustic wave processing device comprising a probe which has a plurality of elements arranged to transmit an acoustic beam, to receive an acoustic echo reflected from an inspection object, and to output an analog element signal according to the received acoustic echo, a transmission unit which uses two or more elements among the plurality of elements as transmission elements and makes the probe transmit the acoustic beam multiple times so as to form a predetermined transmission focal point, a reception unit which receives an acoustic echo corresponding to each transmission of the acoustic beam with two or more elements among the plurality of elements as reception elements, receives analog element signals output from the reception elements, and performs predetermined processing on the analog element signals, an A/D conversion unit which performs A/D conversion on the analog element signals processed by the reception unit to convert the analog element signals to first element data as a digital element signal, a data processing unit which selects two or more pieces of data from a plurality of pieces of first element data output from the A/D conversion unit or a plurality of pieces of first reception data generated by performing phasing addition processing on the first element data and performs superimposition processing on the selected two or more pieces of data to generate processed data, a B mode image generation unit which generates a B mode image based on at least one of the first element data or the processed data generated by the data processing unit, a bloodstream image generation unit which generates a bloodstream image based on bloodstream information included in the first element data, a region setting unit which sets a bloodstream image region where the bloodstream image generation unit generates the bloodstream image, a processing region setting unit which sets a processing region where the data processing unit performs processing based on information relating to the bloodstream image region set by the region setting unit, and a display image generation unit which generates a synthesized image of the B mode image and the bloodstream image based on the information relating to the bloodstream image region set by the region setting unit.

(2) The acoustic wave processing device described in (1), wherein the bloodstream image generation unit calculates the bloodstream information based on a Doppler effect.

(3) The acoustic wave processing device described in (1) or (2), wherein the information relating to the bloodstream image is at least one of the size, position, or shape of the region.

(4) The acoustic wave processing device described in any one of (1) to (3), wherein the processing region setting unit sets a region including a line passing through the bloodstream image region as the processing region.

(5) The acoustic wave processing device described in any one of (1) to (4), wherein the region setting unit sets the bloodstream image region based on an input from an operating unit, and the processing region setting unit sets the processing region to be none while the setting of the bloodstream image region by the operating unit is performed.

(6) The acoustic wave processing device described in any one of (1) to (5), wherein the data processing unit selects two or more pieces of first element data from the plurality of pieces of first element data and superimposes the selected two or more pieces of first element data according to the reception time of an ultrasonic echo received by each element and the position of each element to generate second element data, and the B mode image generation unit generates the B mode image based on the second element data.

(7) The acoustic wave processing device described in any one of (1) to (5), further comprising a phasing addition unit which performs phasing addition on each piece of first element data centering on at least two lines and generates at least two or more pieces of first reception data for each piece of first element data, wherein the data processing unit selects two or more pieces of first reception data from the plurality of pieces of first reception data and superimposes the selected two or more pieces of first reception data according to the reception time of an ultrasonic echo received by each element to generate second reception data, and the B mode image generation unit generates the B mode image based on the second reception data.

(8) The acoustic wave processing device described in (7), wherein the data processing unit superimposes the two or more pieces of first reception data generated from different pieces of first element data and generated through the phasing addition processing in the same line.

(9) The acoustic wave processing device described in any one of (1) to (8), wherein the transmission unit performs at least one of change of a central element or change of a transmission direction of an ultrasound beam to make the probe transmit the ultrasound beam multiple times.

(10) A signal processing method for an acoustic wave processing device, which inspects an inspection object using a probe having a plurality of elements arranged to transmit an acoustic beam, to receive an acoustic echo reflected from the inspection object, and to output an analog element signal according to the received acoustic echo, the signal processing method comprising a transmission step of using two or more elements among the plurality of elements of the probe as transmission elements and making the probe transmit the acoustic beam multiple times so as to form a predetermined transmission focal point, a reception step of receiving an acoustic echo corresponding to each transmission of the acoustic beam with two or more elements among the plurality of elements as reception elements and outputting an analog element signal, an A/D conversion step of performing A/D conversion on the analog element signal processed in the reception step to generate first element data as a digital element signal, a data processing step of selecting two or more pieces of data from a plurality of pieces of first element data output in the A/D conversion step or a plurality of pieces of first reception data generated by performing phasing addition processing on the first element data and performing superimposition processing on the selected two or more pieces of data to generate processed data, a B mode image generation step of generating a B mode image based on at least one of the first element data or the processed data generated in the data processing step, a bloodstream image generation step of generating a bloodstream image based on bloodstream information included in the first element data, a region setting step of setting a bloodstream image region where the bloodstream image is generated in the bloodstream image generation step, a processing region setting step of setting a processing region where processing is performed in the data processing step based on information relating to the bloodstream image region set in the region setting step, and a display image generation step of generating a synthesized image of the B mode image and the bloodstream image based on the information relating to the bloodstream image region set in the region setting step.

(11) A non-transitory computer readable recording medium storing a program which causes a computer to execute a signal processing method for an acoustic wave processing device, which inspects an inspection object using a probe having a plurality of elements arranged to transmit an acoustic beam, to receive an acoustic echo reflected from the inspection object, and to output an analog element signal according to the received acoustic echo, the program causing the computer to execute a transmission step of using two or more elements among the plurality of elements of the probe as transmission elements and making the probe transmit the acoustic beam multiple times so as to form a predetermined transmission focal point, a reception step of receiving an acoustic echo corresponding to each transmission of the acoustic beam with two or more elements among the plurality of elements as reception elements and outputting an analog element signal, an A/D conversion step of performing A/D conversion on the analog element signal processed in the reception step to generate first element data as a digital element signal, a data processing step of selecting two or more pieces of data from a plurality of pieces of first element data output in the A/D conversion step or a plurality of pieces of first reception data generated by performing phasing addition processing on the first element data and performing superimposition processing on the selected two or more pieces of data to generate processed data, a B mode image generation step of generating a B mode image based on at least one of the first element data or the processed data generated in the data processing step, a bloodstream image generation step of generating a bloodstream image based on bloodstream information included in the first element data, a region setting step of setting a bloodstream image region where the bloodstream image is generated in the bloodstream image generation step, a processing region setting step of setting a processing region where processing is performed in the data processing step based on information relating to the bloodstream image region set in the region setting step, and a display image generation step of generating a synthesized image of the B mode image and the bloodstream image based on the information relating to the bloodstream image region set in the region setting step.

According to the invention, it is possible to provide an acoustic wave processing device, a signal processing method, and a non-transitory computer readable recording medium storing a program capable of improving image quality while suppressing degradation of the frame rate and securing real time performance in a color mode, in which a B mode image and a color Doppler image are synthesized and displayed.

BRIEF DESCRIPTION OF THE DRAWINGS

FIG. 4 is a block diagram conceptually showing an example of the configuration of an element data processing unit of the ultrasound diagnostic apparatus shown in FIG. 1.

Parts (a), (b), and (c) of FIG. 8 are conceptual diagrams illustrating element data of a true signal, a delay time of element data, and a superimposition state of element data, parts (d), (e), and (f) of FIG. 8 are conceptual diagrams illustrating element data of ghost, a delay time of element data, and a superimposition state of element data, part (g) of FIG. 8 is a conceptual diagram illustrating a superimposition state of element data corresponding to a plurality of elements, and part (h) of FIG. 8 is a conceptual diagram illustrating a result of superimposition of element data in part (g) of FIG. 8.

Figure 9A:
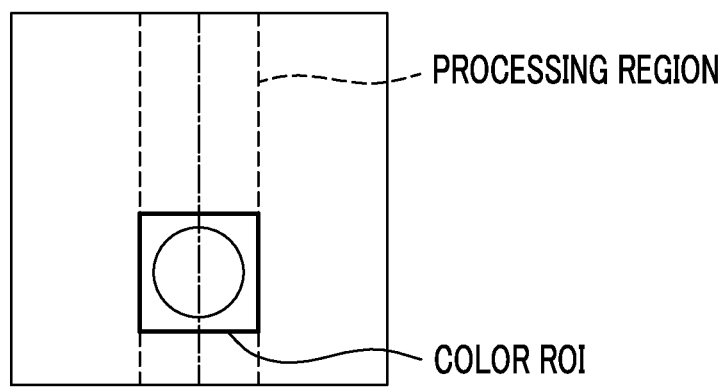
Figure 9B:
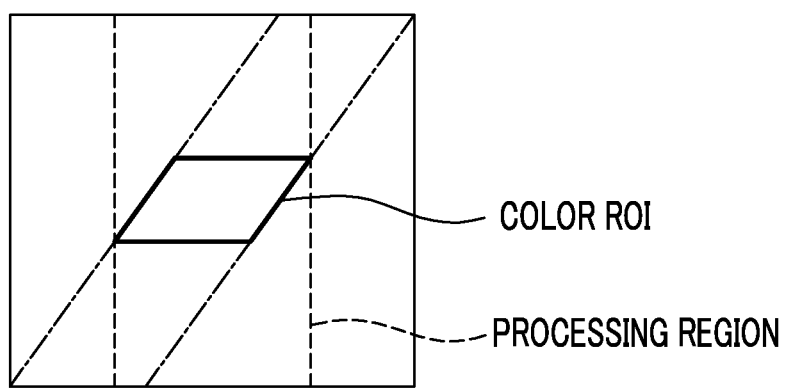

FIGS. 9A and 9B are conceptual diagrams illustrating a processing region.

Figure 1:
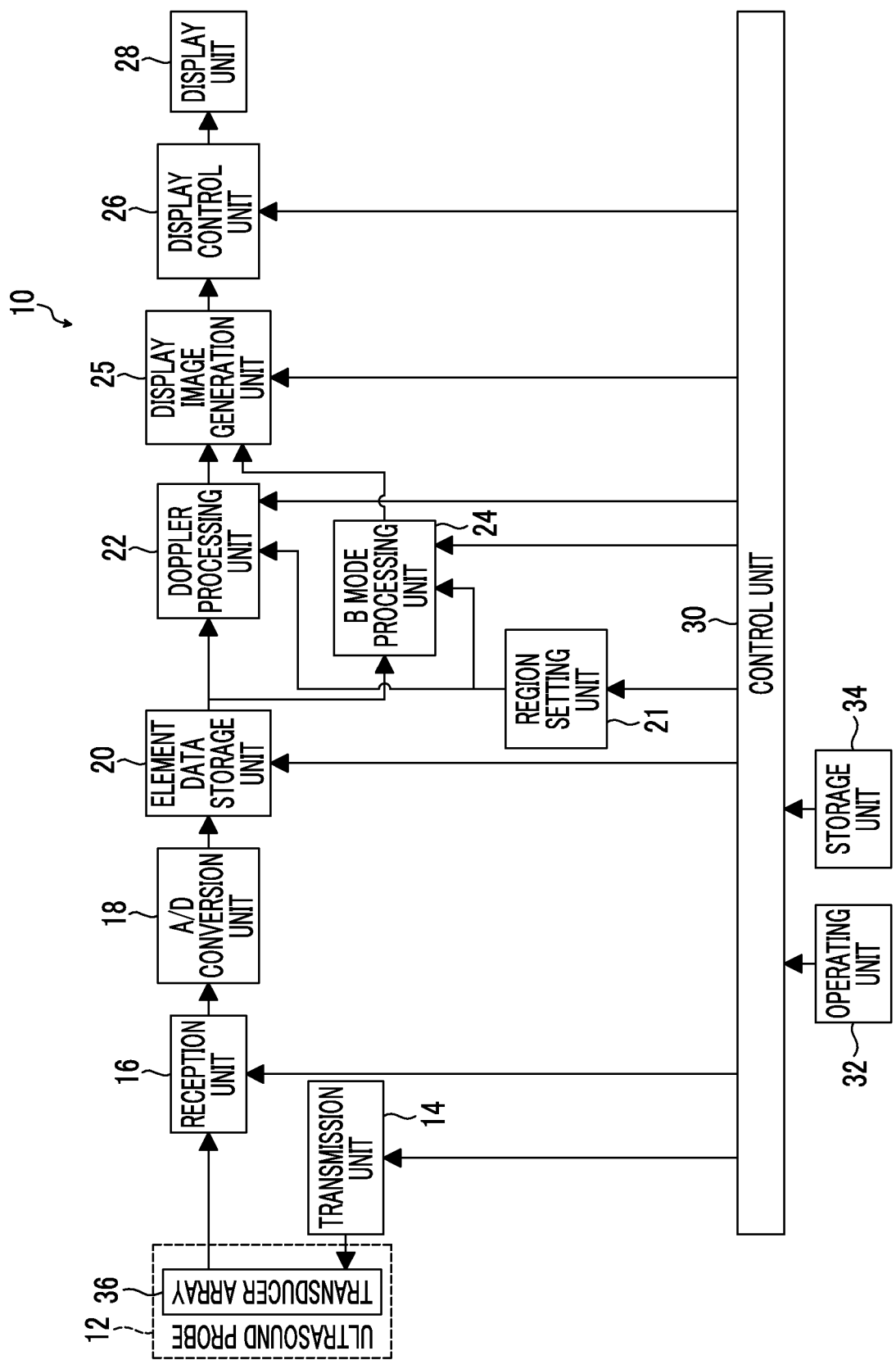
FIG. 1 is a block diagram conceptually showing an example of the configuration of an ultrasound diagnostic apparatus of the invention.
Figure 10:
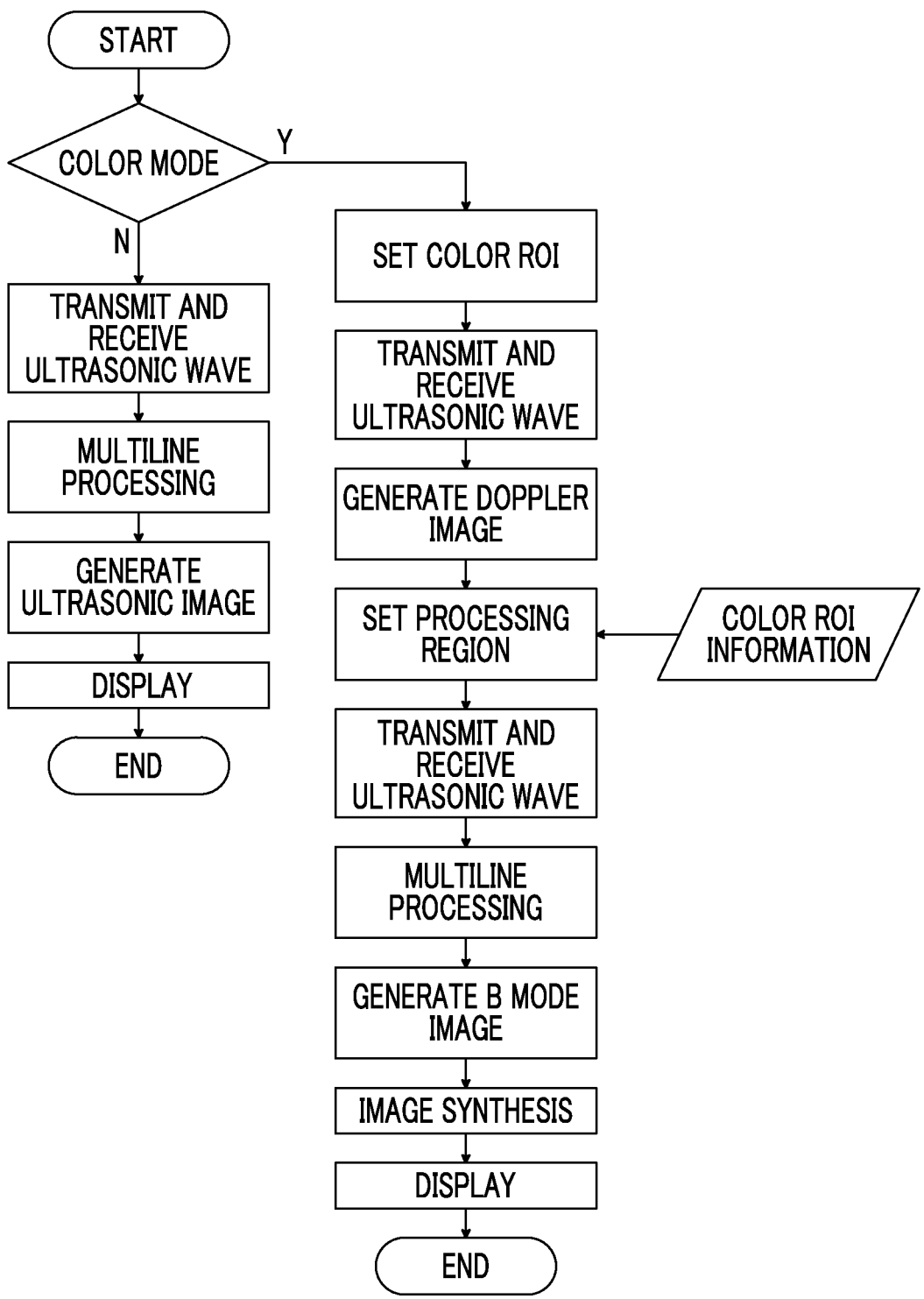

FIG. 10 is a flowchart illustrating the action of the ultrasound diagnostic apparatus shown in FIG. 1.

Figure 11:
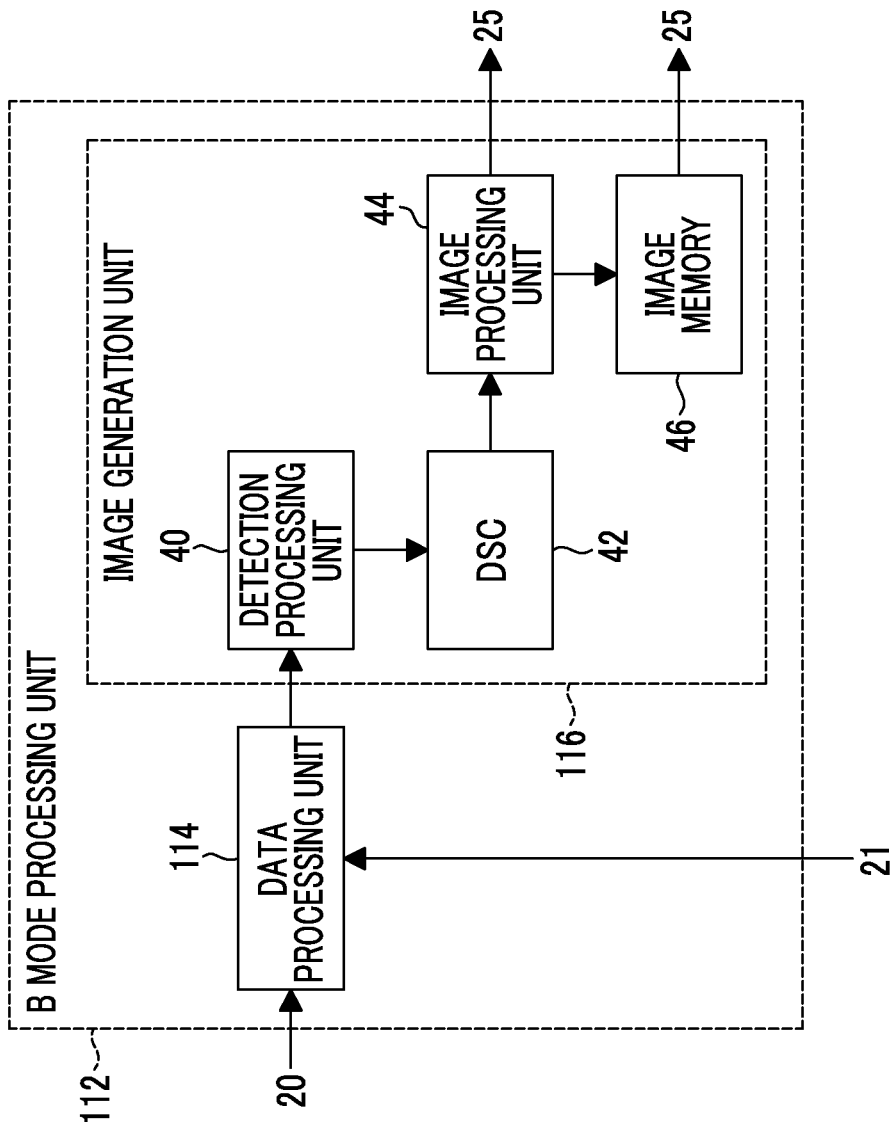

FIG. 11 is a block diagram conceptually showing another example of the configuration of the ultrasound diagnostic apparatus of the invention.

Figure 12:
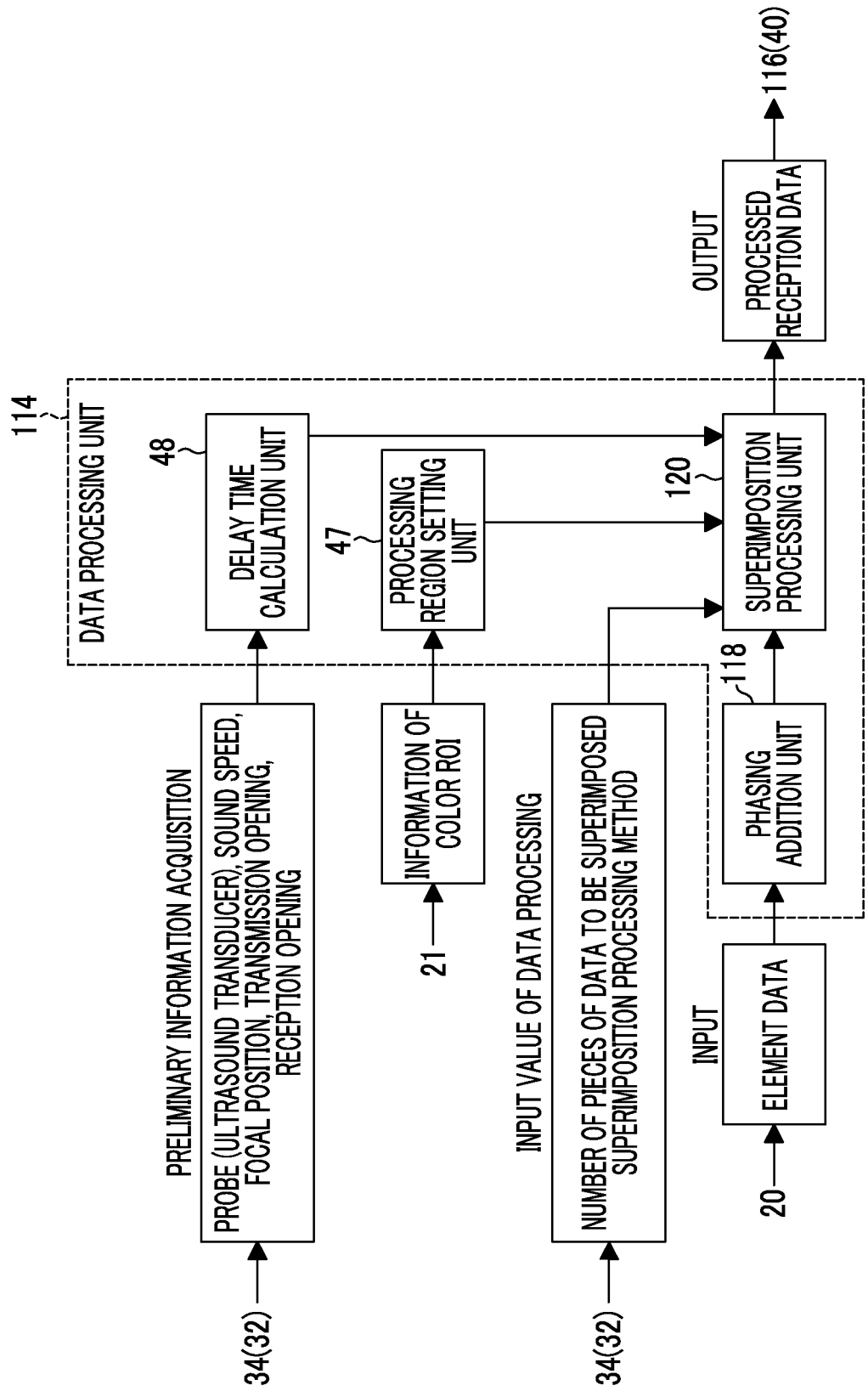

FIG. 12 is a block diagram conceptually showing an example of the configuration of a data processing unit of the ultrasound diagnostic apparatus shown in FIG. 11.

Figure 13:
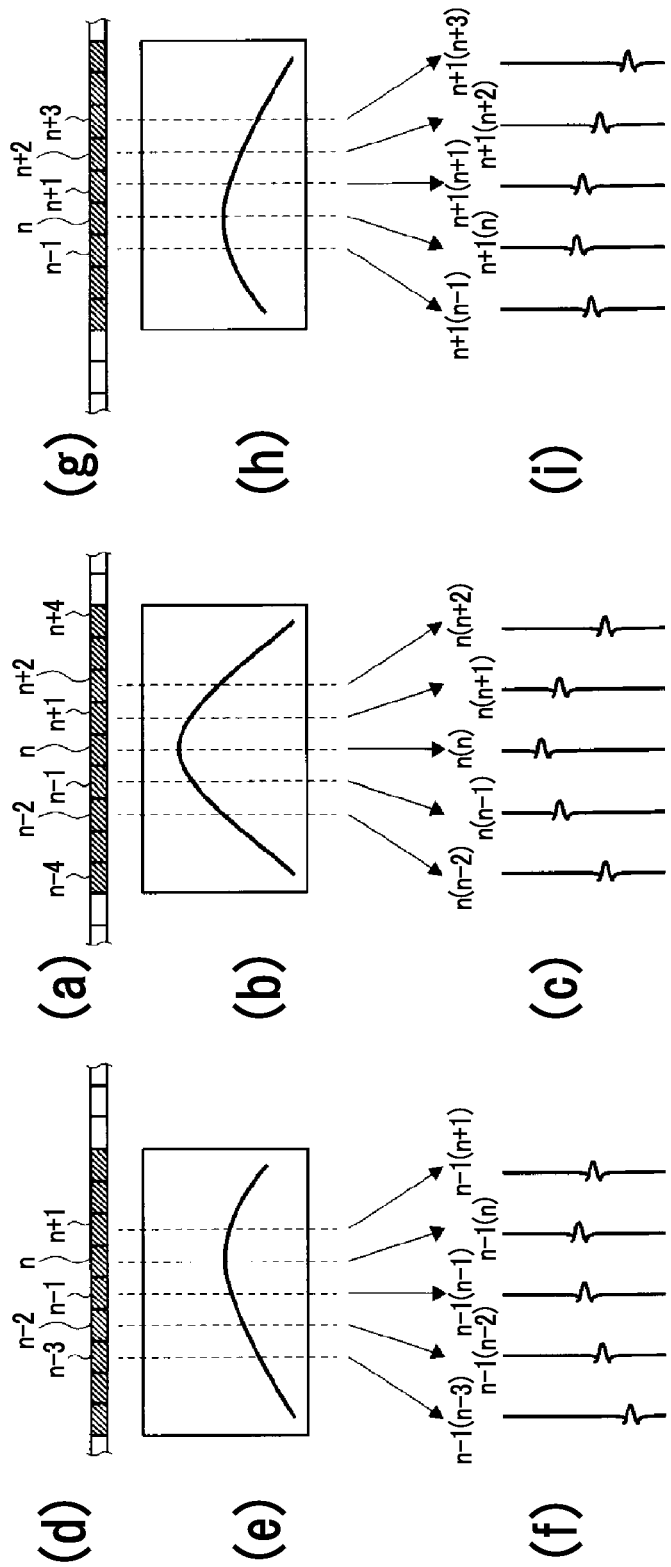

Parts (a), (d), and (g) of FIG. 13 are conceptual diagrams illustrating respective reception elements, parts (b), (e), and (h) of FIG. 13 are conceptual diagrams showing element data obtained by transmission and reception of ultrasonic waves, and parts (c), (f), and (i) of FIG. 13 are conceptual diagrams showing unprocessed reception data obtained by performing phasing addition processing on respective pieces of element data.

Figure 14:
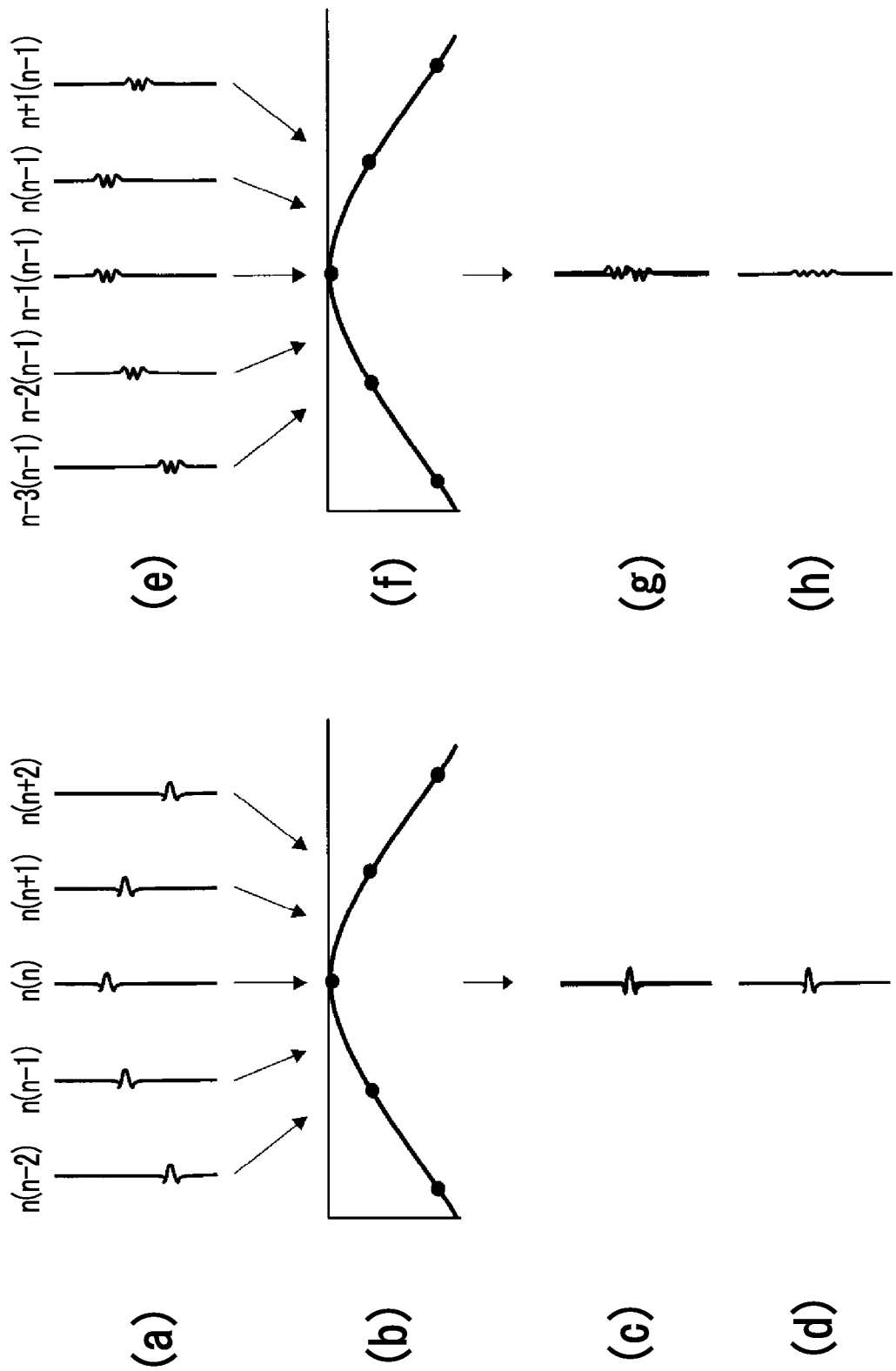

Parts (a) and (e) of FIG. 14 are conceptual diagrams showing unprocessed reception data to be superimposed, parts (b) and (f) of FIG. 14 are conceptual diagrams illustrating a delay time of unprocessed reception data, parts (c) and (g) of FIG. 14 are conceptual diagrams illustrating a state of superimposition of unprocessed reception data, and parts (d) and (h) of FIG. 14 are conceptual diagrams illustrating a result of superimposition of unprocessed reception data.

DESCRIPTION OF THE PREFERRED EMBODIMENTS

Hereinafter, an acoustic wave processing device, a signal processing method, and a non-transitory computer readable recording medium storing a program of the invention will be described in detail based on a preferred first embodiment shown in the accompanying drawings.

In the embodiment of the invention, although an ultrasonic wave is used as an acoustic wave, the invention is not limited to the ultrasonic wave, and an acoustic wave of an audio frequency may be used if an appropriate frequency is selected according to an inspection target, measurement conditions, or the like.

FIG. 1 conceptually shows an example of an ultrasound diagnostic apparatus (acoustic wave processing device) of the invention using a block diagram.

As shown in FIG. 1, an ultrasound diagnostic apparatus 10 has an ultrasound probe 12, a transmission unit 14 and a reception unit 16 connected to the ultrasound probe 12, an A/D conversion unit 18, an element data storage unit 20, a region setting unit 21, a Doppler processing unit 22, a B mode processing unit 24, a display image generation unit 25, a display control unit 26, a display unit 28, a control unit 30, an operating unit 32, and a storage unit 34.

In the example shown in the drawing, the transmission unit 14, the reception unit 16, the A/D conversion unit 18, the element data storage unit 20, the region setting unit 21, an element data processing unit 35, the B mode processing unit 24, the display image generation unit 25, the display control unit 26, the display unit 28, the control unit 30, the operating unit 32, and the storage unit 34 constitute an apparatus body of the ultrasound diagnostic apparatus 10.

The ultrasound diagnostic apparatus 10 includes, as a display mode, a color mode in which a B mode image, which is image information relating to a tissue of a subject based on the strength of an ultrasonic wave reflected from the subject, and a color Doppler image obtained by coloring a two-dimensional Doppler image, which is information relating to movement of a biological tissue (for example, blood) in the subject based on frequency shift information due to a Doppler effect effect included in the reflected ultrasonic wave according to a moving direction or a moving speed of blood are synthesized, and a synthesized ultrasound image is displayed.

The ultrasound diagnostic apparatus 10 may include a display mode other than the color mode, such as a B mode in which a B mode image is displayed alone, or an M mode.

In this specification, the ultrasound image is a B mode image, a color Doppler image, and an image (synthesized image) in which the B mode image and the color Doppler image are synthesized.

The ultrasound probe 12 is a known ultrasound probe which is used in a typical ultrasound diagnostic apparatus.

The ultrasound probe 12 (hereinafter, referred to as a probe 12) has a transducer array 36 in which ultrasound transducers are arranged in a one-dimensional or two-dimensional manner.

The ultrasound transducer transmits an ultrasound beam to a subject in response to a drive signal supplied from the transmission unit 14 when capturing an ultrasound image of an inspection object (hereinafter, referred to as a subject), receives an ultrasonic echo reflected from the subject, and outputs a reception signal according to the strength of the received ultrasonic wave.

Each ultrasound transducer is constituted of a transducer in which electrodes are formed at both ends of a piezoelectric substance made of, for example, piezoelectric ceramic represented by Pb (lead) zirconate titanate (PZT), a polymer piezoelectric element represented by polyvinylidene fluoride (PVDF), piezoelectric single crystal represented by a magnesium niobate-lead titanate solid solution (PMN-PT), or the like.

If a pulsed or continuous-wave voltage is applied to the electrodes of each of the transducers, the piezoelectric substance expands and contracts according to the applied voltage, and a pulsed or continuous-wave ultrasonic wave is generated from each transducer. The ultrasonic waves generated from the respective transducers are converged on a set focal point according to the delay of drive of each transducer and synthesized (that is, transmission-focused) to form an ultrasound beam.

The transducers expand and contract when the ultrasonic echo reflected from the inside of the subject enters, and electrical signals according to the magnitude of expansion and contraction are generated. The electrical signals are output to the reception unit 16 as reception signals (analog element signals).

The transmission unit 14 has, for example, a plurality of pulsers, and supplies a drive signal (applies a drive voltage) to the respective ultrasound transducers of the probe 12.

The transmission unit 14 performs transmission focusing for adjusting the delay amount of the drive signal (the application timing of the drive voltage) based on a transmission delay pattern selected by the control unit 30 such that ultrasonic waves transmitted from a predetermined number (a plurality) of ultrasound transducers form an ultrasound beam converged on the set focal point, and supplies the drive signal to the ultrasound transducers.

With this, an intended ultrasound beam is transmitted from the probe 12 (transducer array 36) to the subject.

The reception unit 16 receives the reception signals output from a predetermined number (a plurality) of ultrasound transducers corresponding to the single transmission of an ultrasound beam in response to a control signal from the control unit 30, performs predetermined processing, such as amplification, on the reception signals, and supplies the reception signals to the A/D conversion unit 18.

In the ultrasound diagnostic apparatus 10 of the invention, a method of transmitting and receiving an ultrasonic wave is basically the same as that in a known ultrasound diagnostic apparatus.

Accordingly, in the single transmission and reception of an ultrasonic wave (transmission of one ultrasound beam and reception of an ultrasonic echo corresponding to the transmission), the number of ultrasound transducers (the number of transmission openings) which generate ultrasonic waves and the number of ultrasound transducers (the number of reception openings) which receive ultrasonic waves (the reception unit 16 receives the reception signals) are not limited as long as the number of ultrasound transducers is plural. In the single transmission and reception, the number of openings may be the same or different between transmission and reception.

In adjacent ultrasound beams in at least an azimuth direction (the arrangement direction of the ultrasound transducers), if transmission regions overlap each other, the number of transmissions and receptions of an ultrasonic wave (the number of sound rays) for forming one ultrasound image or the interval of ultrasound transducers (central elements) to be the center of transmission and reception (that is, the density of scan lines/sound rays) is not limited. Accordingly, transmission and reception of an ultrasonic wave may be performed with all ultrasound transducers corresponding to a region scanned using an ultrasonic wave as a central element, or transmission and reception of an ultrasonic wave may be performed with ultrasound transducers at predetermined intervals, for example, at every two or every four ultrasound transducers, as a central element.

Similarly to a known ultrasound diagnostic apparatus, in a case of a color mode in which a B mode image and a color Doppler image are synthesized and displayed, the generation of the B mode image and the generation of the color Doppler image are sequentially performed for every frame, and a synthesized ultrasound image in which the B mode image and the color Doppler image are synthesized is generated.

In a case of generating the B mode image, in order to form one B mode image, transmission and reception are performed at a plurality of positions (lines) while sequentially moving transmission and reception positions. In a case of generating the Doppler image, in order to form one Doppler image, transmission and reception are performed multiple times in the same direction.

The A/D conversion unit 18 performs analog/digital conversion on the analog reception signals supplied from the reception unit 16 to element data (first element data) as digital reception signals.

The A/D conversion unit 18 supplies element data subjected to A/D conversion to the element data storage unit 20.

The element data storage unit 20 sequentially stores element data supplied from the A/D conversion unit 18. The element data storage unit 20 stores information (for example, the depth of a reflection position of an ultrasonic wave, the density of scan lines, and a parameter indicating a visual field width) relating to a frame rate input from the control unit 30 in association with the respective pieces of element data.

Preferably, the element data storage unit 20 stores all pieces of element data corresponding to at least one ultrasound image (an ultrasound image of one frame) and does not erase element data of the ultrasound image during display and before display until at least the display of the ultrasound image ends.

The region setting unit 21 is a unit which sets a region where a color Doppler image is generated, that is, a bloodstream image region when the color mode is selected as the display mode. In the following description, the bloodstream image region is also referred to as a color region ROI.

A method of setting a color region ROI in the region setting unit 21 is not particularly limited, and various known color region ROI setting method are available.

For example, if an operator selects the color mode, a frame indicating a color region ROI is displayed on an ultrasound image (B mode image) displayed on the display unit 28 in a superimposed manner. The operator operates the operating unit 32 while viewing the ultrasound image displayed on the display unit 28, and moves, reduces and enlarges, or deforms the frame indicating the ROI displayed on the ultrasound image in a superimposed manner to indicate the position, size, and shape of the color region ROI. The region setting unit 21 sets the color region ROI based on an input operation from the operating unit 32.

At this time, for example, a case where an instruction indicating the determination of the color region ROI is input may be regarded that the color region ROI is set, or a case where the frame indicating the ROI is stopped for a predetermined time (for a predetermined number of frames) may be deemed that the color region ROI is set. Alternatively, the time when an operation to set the color region ROI starts may be regarded that the color region ROI is set.

Even in a case where the operator performs an operation to change the position of the color region ROI during the display of the ultrasound image in the color mode, similarly to the above, the frame indicating the color region ROI may be displayed, and the operator may operate the operating unit 32 and may move, reduce and enlarge, and deform the frame indicating the ROI to set the color region ROI.

The region setting unit 21 supplies information relating to the set color region ROI to the Doppler processing unit 22 and the B mode processing unit 24

The Doppler processing unit 22 is a unit which generates the color Doppler image of the color region ROI from element data stored in the element data storage unit based on information relating to the color region ROI set by the region setting unit 21 when the color mode is selected as the display mode.

Specifically, the Doppler processing unit 22 performs frequency analysis on element data to generate Doppler data representing a relative moving speed of the subject and the ultrasound probe 12. If C represents a sound speed, V represents a relative moving speed of the ultrasound probe 12 and a biological tissue in a direction in which an ultrasonic wave travels, a frequency of a transmitted ultrasonic wave is fs, and a frequency of a received ultrasonic wave is fr, the following relationship is established.

$$fr = fs \cdot (C+V)/(C-V) = fs + 2V/(C-V) \cdot fs \approx fs + 2V/C \cdot fs \quad (1)$$

Here, if a Doppler transition frequency transition frequency is $\Delta f(=fr-fs)$, the following expression is obtained from Expression (1).

$$\Delta f = (2V/C) \cdot fs \quad (2)$$

Accordingly, if Expression (2) is converted to $V = \Delta f \cdot C/2/fs$, it is understood that the moving speed V is determined from the Doppler transition frequency $\Delta f$. The Doppler processing unit 22 performs frequency analysis on element data to calculate the Doppler transition frequency $\Delta f$ and acquires information relating to the relative moving speed V of the biological tissue with respect to the ultrasound probe 12 as Doppler data. Doppler data is generated at a plurality of sample points in the color region ROI set by the region setting unit 21.

The Doppler processing unit 22 converts each piece of Doppler data of each sample point to color information using a speed conversion scale designated in advance and performs predetermined processing on the color information to generate color Doppler image data.

The Doppler processing unit 22 supplies the generated color Doppler image data to the display image generation unit 25.

In this embodiment, although a configuration in which the Doppler processing unit 22 generates a bloodstream image based on a Doppler effect has been made, the invention is not limited thereto, and a configuration in which a bloodstream image is generated by various known methods, such as a power Doppler method, may be made.

The B mode processing unit 24 is a unit which reads element data stored in the element data storage unit 20 under the control of the control unit 30 and generates a B mode image.

Figure 2:
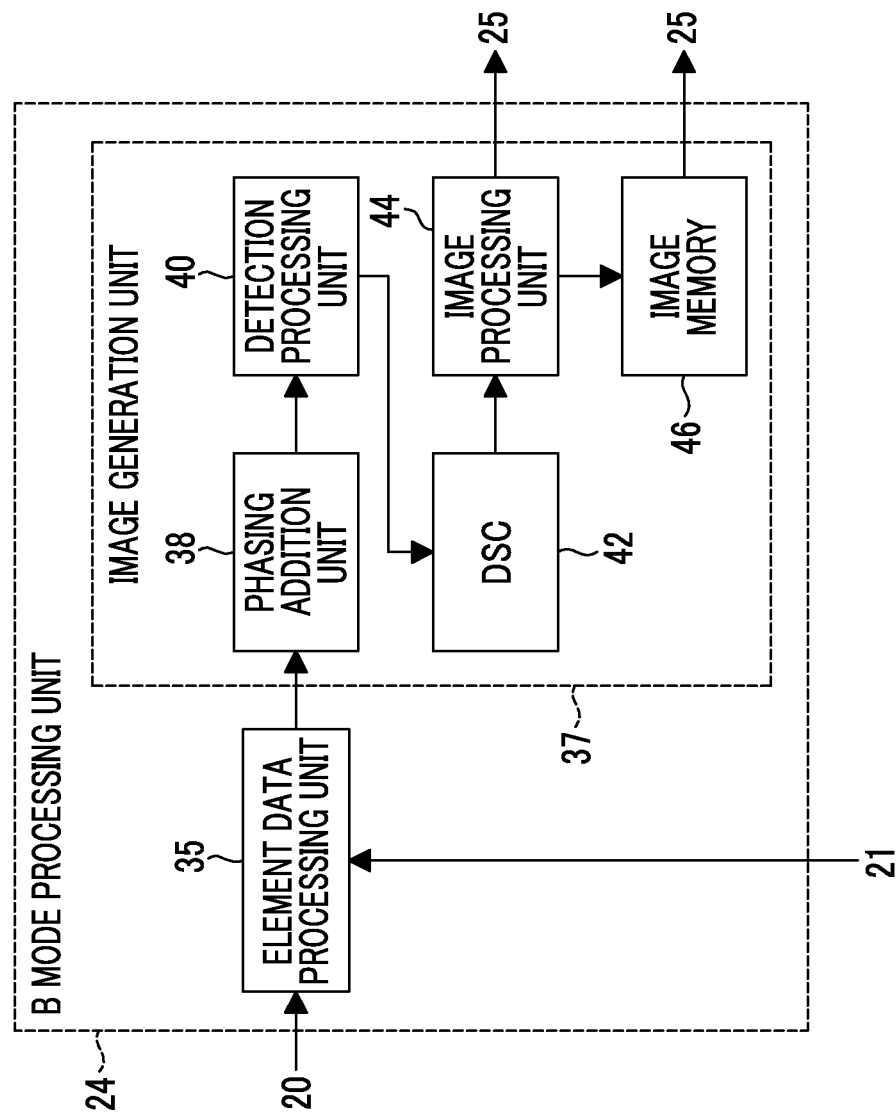
FIG. 2 is a block diagram conceptually showing an example of the configuration of a B mode processing unit of the ultrasound diagnostic apparatus shown in FIG. 1.

As shown in FIG. 2, the B mode processing unit 24 has an element data processing unit 35 and an image generation unit 37.

The element data processing unit 35 is a unit which superimposes element data and generates processed element data (second element data) corresponding to each piece of element data.

Specifically, the element data processing unit 35 superimposes element data obtained by transmission of a predetermined number (a plurality) of ultrasound beams, for which the ultrasound transducers (elements (central elements) to be the center) to be the center are different and the transmission regions of the ultrasound beams overlap each other, among element data stored in the element data storage unit 20 based on information relating to the processing region from the region setting unit 21 under the control of the control unit 30 according to the time (delay time) when each ultrasound transducer receives an ultrasonic echo and the positions of the ultrasound transducers, and generates processed element data corresponding to element data (element data of an element of interest described below).

The processing in the element data processing unit 35 will be described below in detail.

The element data processing unit 35 sends the generated processed element data to the image generation unit 37.

The image generation unit 37 generates reception data (sound ray signal) from unprocessed element data or processed element data supplied from the element data processing unit 35 under the control of the control unit 30 and generates a B mode image from reception data.

The same processing is performed in the image generation unit 37 regardless of unprocessed element data and processed element data.

The image generation unit 37 has a phasing addition unit 38, a detection processing unit 40, a digital scan converter (DSC) 42, an image processing unit 44, and an image memory 46.

The phasing addition unit 38 performs reception focusing processing by performing phasing addition unprocessed element data or processed element data generated by the element data processing unit 35, and generates reception data.

As described above, the transducer array 36 of the probe 12 has a plurality of elements (ultrasound transducers) arranged in a one-dimensional or two-dimensional manner. Accordingly, the distance to one reflection point in the subject is different by ultrasound transducer. For this reason, even in an ultrasonic echo reflected at the same reflection point, the time at which the ultrasonic echo reaches each ultrasound transducer is different. The phasing addition unit 38 delays each signal of processed element data by an amount corresponding to the difference (delay time) in the reaching time of the ultrasonic echo in the respective ultrasound transducers, according to a reception delay pattern selected by the control unit 30, performs reception focusing processing in a digital manner by performing phasing addition processed element data assigned with the delay time, and generates reception data.

The phasing addition unit 38 supplies the generated reception data to the detection processing unit 40.

Figure 3:
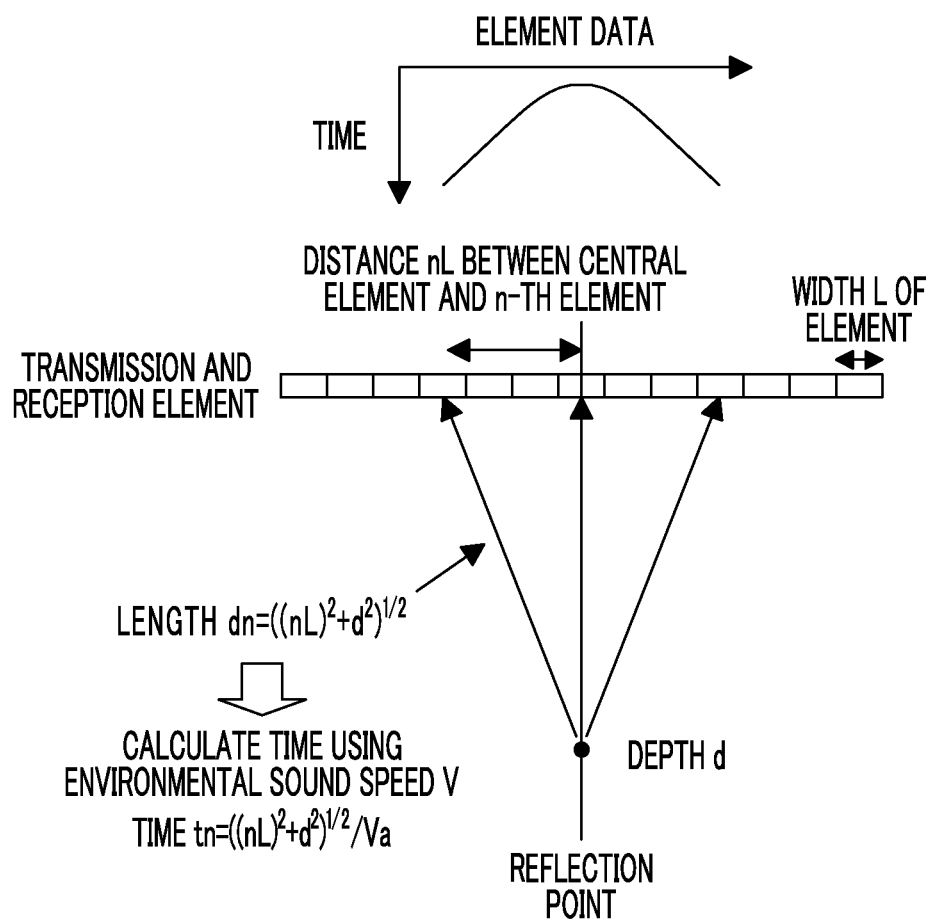
FIG. 3 is a conceptual diagram illustrating an example of reception focusing processing in the ultrasound diagnostic apparatus shown in FIG. 1.

FIG. 3 shows an example of the reception focusing processing.

FIG. 3 shows a case of a linear probe in which a plurality of ultrasound transducers of the probe 12 are arranged in a line in a right-left direction of the drawing. However, in a case of a convex probe, the probe shape is different, but a way of thinking may be the same.

If the width of each ultrasound transducer in the azimuth direction is L, the distance between the central ultrasound transducer in the azimuth direction and an n-th ultrasound transducer toward an end portion becomes nL.

As shown in the drawing, if a reflection point of an ultrasonic wave is positioned at a distance (depth) d vertical to the arrangement direction from the central ultrasound transducer, the distance (length) $d_r$ between the n-th ultrasound transducer and the reflection point is calculated by Expression (3).

$$d_n = ((nL)^2 d^2)^{1/2} \qquad (3)$$

Accordingly, the time $t_n$ at which an ultrasonic echo reaches (is received by) the n-th ultrasound transducer from the reflection point is calculated by Expression (4) using a sound speed (environmental sound speed) Va of an ultrasonic wave in the subject.

$$t_n = d_n/Va = ((nL)^2 + d^2)^{1/2}/Va \qquad (4)$$

As described above, the distance between the ultrasound transducer and the reflection point is different for each ultrasound transducer. For this reason, in this example, as shown in a graph on the upper side of the drawing, the reaching time $t_n$ of the ultrasonic echo becomes longer as the ultrasound transducer is closer to the end portion in the arrangement direction.

Specifically, if the time until an ultrasonic wave is received by the central ultrasound transducer from the reflection point is $t_1$, an ultrasonic wave received by the n-th ultrasound transducer is delayed by the time $\Delta t = t_n - t_1$ with respect to an ultrasonic wave received by the central ultrasound transducer. In this example, the delay time $\Delta t$ is, that is, a reception delay pattern.

The phasing addition unit 38 performs phasing addition on the signals corresponding to the respective ultrasound transducers using the delay time represented by the time $\Delta t$ and performs reception focusing processing to generate reception data.

The detection processing unit 40 performs correction of attenuation depending on the distance according to the depth of the reflection point of the ultrasonic wave on reception data generated by the phasing addition unit 38, and then performs envelope detection processing to generate B mode image data which is tomographic image information (luminance image information) in the subject.

The DSC 42 converts (raster-converts) B mode image data generated in the detection processing unit 40 to image data corresponding to a typical television signal scan system.

The image processing unit 44 performs various kinds of necessary image processing, such as gradation processing, on B mode image data input from the DSC 42 to generates B mode image data which is used for display. The image processing unit 44 outputs B mode image data subjected to the image processing to the display image generation unit 25 or the display control unit 26 and/or stores B mode image data in the image memory 46.

The image memory 46 is known storage means (storage medium) which stores B mode image data processed by the image processing unit 44. B mode image data stored in the image memory 46 is read to the display control unit 26 for display on the display unit 28 as necessary. Alternatively, B mode image data is read to the display image generation unit 25 for generation of a synthesized image.

In a case of the color mode, the display image generation unit 25 is a unit which synthesizes color Doppler image data generated by the Doppler processing unit 22 and B mode image data generated by the B mode processing unit 24 to generate synthesized image data for display.

A synthesis method of the B mode image data and the color Doppler image data is not particularly limited, and various synthesis methods which are performed by a known ultrasound diagnostic apparatus are available. For example, synthesized image data may be generated such that the B mode image is represented by luminance and the Doppler image is represented by chromaticity.

The display image generation unit 25 outputs the generated synthesized image data to the display control unit 26.

The display control unit 26 makes the display unit 28 display the synthesized ultrasound image using synthesized image data generated by the display image generation unit 25 in the color mode. In a case where a mode other than the color mode is selected as the display mode, an image according to the selected display mode is displayed on the display unit 28. For example, in a case where the B mode is selected as the display mode, the B mode image generated by the B mode processing unit 24 is displayed.

The display unit 28 includes, for example, a display device, such as an LCD, and displays the ultrasound image under the control of the display control unit 26.

The control unit 30 is a unit which performs various kinds of control of the ultrasound diagnostic apparatus 10 based on a command input by the operator using the operating unit 32.

The control unit 30 supplies various kinds of information input by the operator using the operating unit 32 to necessary units. For example, in a case where information necessary for setting the color region ROI used in the region setting unit 21, information necessary for generating the color Doppler image used in the Doppler processing unit 22, information necessary for calculating the delay time used in the element data processing unit 35 and the phasing addition unit 38 of the image generation unit 37, and information necessary for processing element data in the element data processing unit 35 are input using the operating unit 32, these kinds of information are supplied to the respective units including the transmission unit 14, the reception unit 16, the element data storage unit 20, the region setting unit 21, the Doppler processing unit 22, the element data processing unit 35, the image generation unit 37, the display control unit 26, and the like as necessary.

In a case where the operator performs an input to select the display mode using the operating unit 32, the control unit 30 controls the respective units of the ultrasound diagnostic apparatus 10 according to the display mode.

The operating unit 32 is used when the operators performs an input operation, and includes a keyboard, a mouse, a trackball, a touch panel, and the like.

The operating unit 32 includes an input function of allowing the operator to input various kinds of information as necessary. For example, the operating unit 32 includes an input function of inputting information relating to the probe 12 (ultrasound transducers), the transmission opening and the reception opening in the probe 12 (transducer array 36), information relating to the generation of processed element data, such as the number of pieces of element data to be superimposed or a superimposition method, the focal position of an ultrasound beam, and the like. Furthermore, the operating unit 32 includes an input function of inputting information for setting the color region ROI. Furthermore, the operating unit 32 includes an input function of selecting the display mode.

These kinds of information are input, for example, by selection of an imaging region (diagnosis region), selection of image quality, selection of the depth of an ultrasound image to be captured, and the like.

The storage unit 34 stores an operation program for allowing the control unit 30 to control the respective units of the ultrasound diagnostic apparatus 10, the transmission delay pattern and the reception delay pattern, information relating to the generation of processed element data, information necessary for allowing the control unit 30 to operate or control the ultrasound diagnostic apparatus, such as information relating to the probe 12, the transmission opening and the reception opening, and information relating to the focal position input from the operating unit 32.

For the storage unit 34, known recording mediums, such as a hard disk, a flexible disk, an MO, an MT, a RAM, a CD-ROM, and a DVD-ROM, are available.

In the ultrasound diagnostic apparatus 10, the region setting unit 21, the Doppler processing unit 22, the element data processing unit 35, the phasing addition unit 38, the detection processing unit 40, the DSC 42, the image processing unit 44, the display control unit 26, and the like are constituted of a CPU and an operation program which causes the CPU to perform various kinds of processing. However, in the invention, these units may be constituted using digital circuits.

As described above, the element data processing unit 35 is a unit which superimposes element data obtained by transmission of a predetermined number (a plurality) of ultrasound beams, for which the ultrasound transducers (central elements) to be the center are different and the transmission regions of the ultrasound beams overlap each other, among element data (unprocessed element data) stored in the element data storage unit 20 according to the time received by each ultrasound transducer and the positions of the ultrasound transducers to generate processed element data.

In the following description, the ultrasound transducers are also simply referred to as "elements".

FIG. 4 conceptually shows the configuration of the element data processing unit 35 using a block diagram.

As shown in FIG. 4, the element data processing unit 35 has a processing region setting unit 47, a delay time calculation unit 48, and a superimposition processing unit 49.

The processing region setting unit 47 is a unit which sets a processing region where the superimposition processing unit 49 performs superimposition processing based on information relating to the color region ROI set by the region setting unit 21.

Specifically, the processing region setting unit 47 sets a region including a line passing through the color region ROI as a processing region based on information relating to the position, size, and shape of the color region ROI.

A setting method of a processing region in the processing region setting unit 47 will be described below in detail.

The processing region setting unit 47 supplies information relating to the set processing region to the superimposition processing unit 49.

The delay time calculation unit 48 acquires information relating to the probe 12 (ultrasound transducers (elements)), the focal position of the ultrasound beam, a position of a sampling point (an output position of element data), the transmission opening and the reception opening of the probe 12, and the like input from the operating unit 32 or input from the operating unit 32 and stored in the storage unit 34 in advance.

The delay time calculation unit 48 calculates a delay time of an ultrasonic echo received by the element of the reception opening, that is, element data based on the geometrical positions of the element of the transmission opening which oscillates an ultrasonic wave to transmit (generate) an ultrasound beam and the element of the reception opening which receives an ultrasonic echo from the subject.

The delay time calculation unit 48 supplies information relating to the calculated delay time to the superimposition processing unit 49.

The superimposition processing unit 49 reads element data (element data obtained by the ultrasound beams where the central elements are different and the transmission regions overlap each other (two or more pieces of element data generated in two or more target regions)) to be superimposed from element data stored in the element data storage unit 20 based on information relating to the processing region supplied from the processing region setting unit 47 and information relating to element data processing, such as the number of pieces of element data to be superimposed and a superimposition processing method, input from the operating unit 32 or input from the operating unit 32 and stored in the storage unit 34.

The superimposition processing unit 49 superimposes two or more of pieces of element data based on the delay time corresponding to each piece of element data calculated by the delay time calculation unit 48 on the reception time, that is, according to the time and according to the received absolute position of the element of the probe to generate processed element data.

In the ultrasound diagnostic apparatus 10 of this embodiment, in a case of the color mode, the superimposition processing unit 49 performs element data superimposition processing in the processing region set by the processing region setting unit 47 and does not perform superimposition processing in other regions.

Hereinafter, processing of element data in the element data processing unit 35 will be described below in detail.

First, in the ultrasound probe 12, in a case where an ultrasound beam is transmitted from a transmission opening, that is, an element (hereinafter, simply referred to as a transmission element), which sends an ultrasonic wave to transmit an ultrasound beam, to a subject, and an ultrasonic echo generated by an interaction with the subject is received by a reception opening, that is, an element (hereinafter, simply referred to as a reception element) which receives an ultrasonic echo to obtain element data, the relationship between the ultrasound beam from the transmission element and element data obtained by the reception element will be described.

Figure 5B:
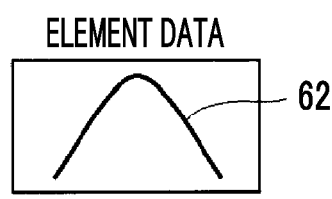
FIGS. 5B and 5D are conceptual diagrams showing element data obtained by transmission and reception of ultrasonic waves.
Figure 5D:
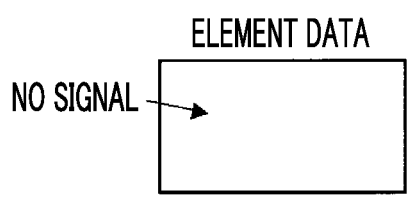
Figure 5A:
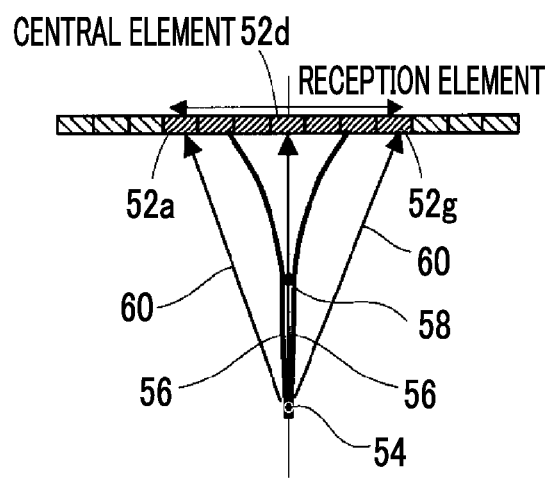
FIGS. 5A and 5C are conceptual diagrams illustrating transmission and reception of ultrasonic waves by an ideal ultrasound beam.

As an example, as shown in FIG. 5A, an ultrasound beam is transmitted with three elements centering on the central element 52d as a transmission element, and an ultrasonic echo is received with seven elements centering on the central element 52d and elements 52a and 52g as both end as a reception element. Next, as shown in FIG. 5C, the elements are moved (hereinafter, also referred to as shifted) in the azimuth direction for one element, an ultrasound beam is transmitted with three elements 52d to 52f as a transmission element, and an ultrasonic echo is received with seven elements 52b to 52h as a reception element to acquire element data.

At this time, an ideal case where an ultrasound beam 56 which is transmitted to an inspection region including a reflection point 54 is converged on a focal point 58 and is narrowed to an element interval or less is considered.

As in FIG. 5A, the element 52d directly above the reflection point 54 (on a straight line connecting the reflection point and the focal point) is used as a central element, the ultrasound beam 56 is transmitted from the three elements centering on the central element 52d as a transmission element, and the ultrasonic echo is received by the seven elements centering on the central element 52d and elements 52a and 52g as both end as a reception element to acquire element data, the focal point 58 of the ultrasound beam 56 is on a straight line connecting the element 52d as a central element and the reflection point 54. In this case, since the ultrasound beam 56 is transmitted to the reflection point 54, the ultrasonic echo reflected from the reflection point 54 is generated.

Figure 5C:
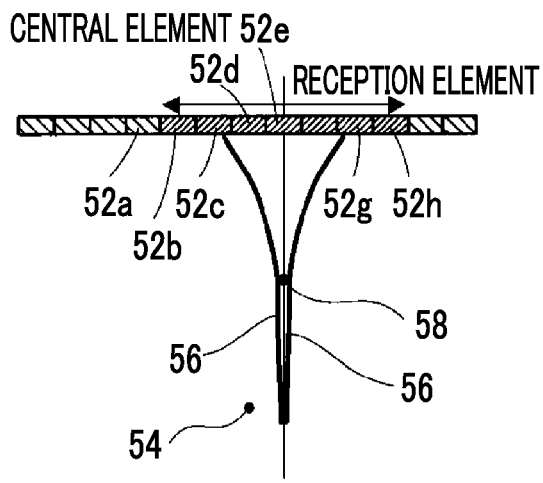

In contrast, as shown in FIG. 5C, in a case where the central element is shifted for one element, the element 52e adjacent to the element 52d directly above the reflection point 54 becomes a central element.

The element 52e is used as a central element, the ultrasound beam 56 is transmitted from the elements 52d to 52f as a transmission element, and the ultrasonic echo is received by the elements 52b to 52h as a reception element.

At this time, similarly, if the ultrasound beam 56 is ideal, the reflection point 54 does not exist in the transmission direction of the ultrasound beam 56, that is, on a straight line connecting the central element 52e and the focal point 58. Accordingly, the ultrasound beam 56 is not transmitted to the reflection point 54.

For this reason, the ultrasonic echo reflected from the reflection point 54 is not generated, and the elements 52b to 52h as a reception element do not receive the ultrasonic echo from the reflection point 54; thus, as shown in FIG. 5D, element data including no reflection signal from the reflection point is obtained (the signal strength of element data becomes "0").

Figure 6B:
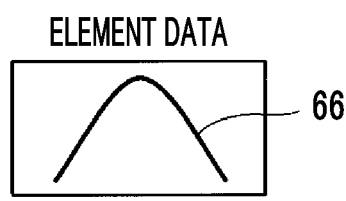
FIGS. 6B and 6D are conceptual diagrams showing element data obtained by transmission and reception of ultrasonic waves.
Figure 6D:
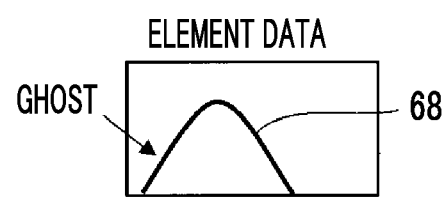
Figure 6A:
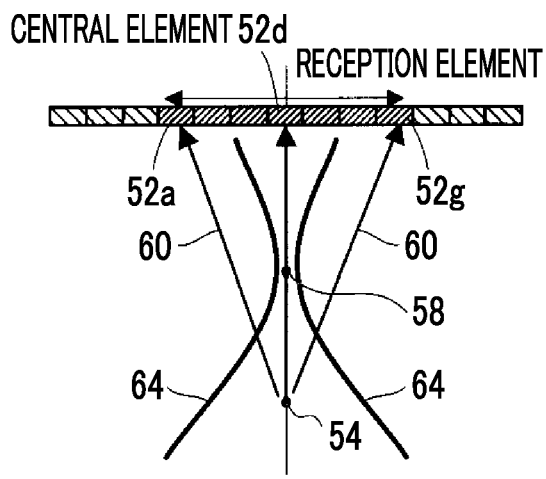
FIGS. 6A and 6C are conceptual diagrams illustrating transmission and reception of ultrasonic waves by an actual ultrasound beam.
Figure 6C:
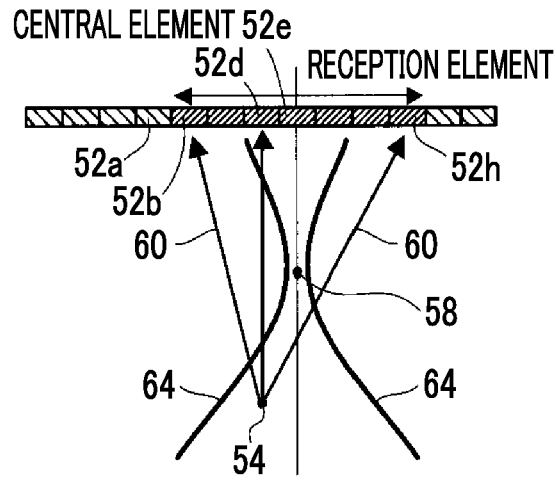

However, since an actual ultrasound beam is converged on the focal point 58 and then diffused like an ultrasound beam 64 shown in FIGS. 6A and 6C, the width is larger than the element interval.

Similarly to FIG. 5A, as in FIG. 6A, in a case where the element 52d directly above the reflection point 54 is used as a central element, and an ultrasound beam 64 is transmitted with the elements 52c to 52e as a transmission element, even if the ultrasound beam 56 has a large width, the focal point 58 is on a straight line connecting the element 52d and the reflection point 54. Accordingly, the ultrasound beam 64 is reflected from the reflection point 54, and the ultrasonic echo is generated.

As a result, similarly to the case of FIG. 5A, the ultrasonic echo from the reflection point 54 is received by the elements 52a to 52g as a reception element through a reception path 60 which expands at a predetermined angle, and similarly, element data 66 (hereinafter, for convenience, referred to as "true element data") including a true signal shown in FIG. 6B is obtained.

Next, similarly to FIG. 5C, as shown in FIG. 6C, the central element is shifted for one element, the adjacent element 52e is used as a central element, the ultrasound beam 56 is transmitted with the elements 52d to 52f as a transmission element, and the ultrasonic echo is received with the elements 52b to 52h as a reception element. In this case, since the ultrasound beam 64 has a large width, even if the reflection point 54 does not exist in the transmission direction of the ultrasonic wave, that is, on a straight line connecting the element 52e as a central element and the focal point 58, the ultrasound beam 64 is transmitted to (reaches) the reflection point 54.

For this reason, an ultrasonic echo, so-called a reflection echo of ghost, which does not originally exist, is generated from the reflection point 54 in the transmission direction of the ultrasound beam. As shown in FIG. 6C, the reflection echo of ghost from the reflection point 54 is received by the elements 52b to 52h as a reception element through the reception path 60 which expands at a predetermined angle. As a result, element data 68 (hereinafter, for convenience, referred to as "element data of ghost") including a ghost signal shown in FIG. 6D is obtained by the elements 52b to 52h.

Such element data 68 of ghost causes degradation of the accuracy of an ultrasound image generated from element data.

The element data processing unit 35 calculates a delay time corresponding to element data using the delay time calculation unit 48, and the superimposition processing unit 49 superimposes two or more pieces of element data according to the delay time and the absolute position of the element, whereby processed element data which is high-accuracy element data with a true signal enhanced and a ghost signal attenuated is generated.

As described above, the delay time calculation unit 48 calculates the delay time of element data received by each of the reception elements (reception openings).

That is, the propagation distance of the ultrasound beam 64 shown in FIG. 6C is the sum of a transmission path along which the ultrasound beam 64 reaches the reflection point 54 from the element 52e as a central element through the focal point 58 and a reception path along which the reflection echo of ghost reaches each of the elements 52b to 52h as a reception element from the reflection point 54.

The propagation distance of the ultrasound beam 64 shown in FIG. 6C becomes longer than the propagation distance of the ultrasound beam 64 shown in FIG. 6A, that is, the sum of a transmission path along which the ultrasound beam 64 reaches the reflection point 54 from the central element 52d through the focal point 58 and a reception path along which a true ultrasonic echo reaches the elements 52a to 52g as a reception element from the reflection point 54.

For this reason, element data 68 of ghost shown in FIG. 6D is delayed with respect to true element data 66 shown in FIG. 6B.

In the delay time calculation unit 48 of the element data processing unit 35, the time difference between element data of ghost and true element data, that is, the delay time is calculated from a sound speed, the transmission elements, the focal point of the ultrasound beam, the reflection point of the subject, and the geometrical arrangement of the reception elements.

Accordingly, the calculation of the delay time requires information relating to the shape (element interval, linear shape, convex shape, or the like) of the probe 12, the sound speed, the position of the focal point, the transmission opening, the reception opening, and the like. In the delay time calculation unit 48, these kinds of information input from the operating unit 32 or stored in the storage unit 34 are acquired to perform the calculation of the delay time.

For the sound speed, a fixed value (for example, 1540 m/sec) may be used, in a case where a sound speed calculation unit is provided, a sound speed (environmental sound speed) calculated by the sound speed calculation unit may be used, or a sound speed may be input by the operator.

As described above, in a case where a processing condition change unit 23 changes the value of the sound speed, the delay time calculation unit 48 calculates a delay time using the value of the sound speed set by the processing condition change unit 23.

The delay time can be calculated from the difference between the total length (propagation distance) of the transmission path of the ultrasound beam reaching the reflection point from the transmission element through the focal point and the reception path of the true reflection ultrasonic echo or the reflection signal of ghost reaching the reception element from the reflection point calculated from the transmission elements, the focal point of the ultrasound beam, the reflection point of the subject, and the geometrical arrangement of the reception elements, and a propagation time calculated by the sound speed.

Figure 7A:
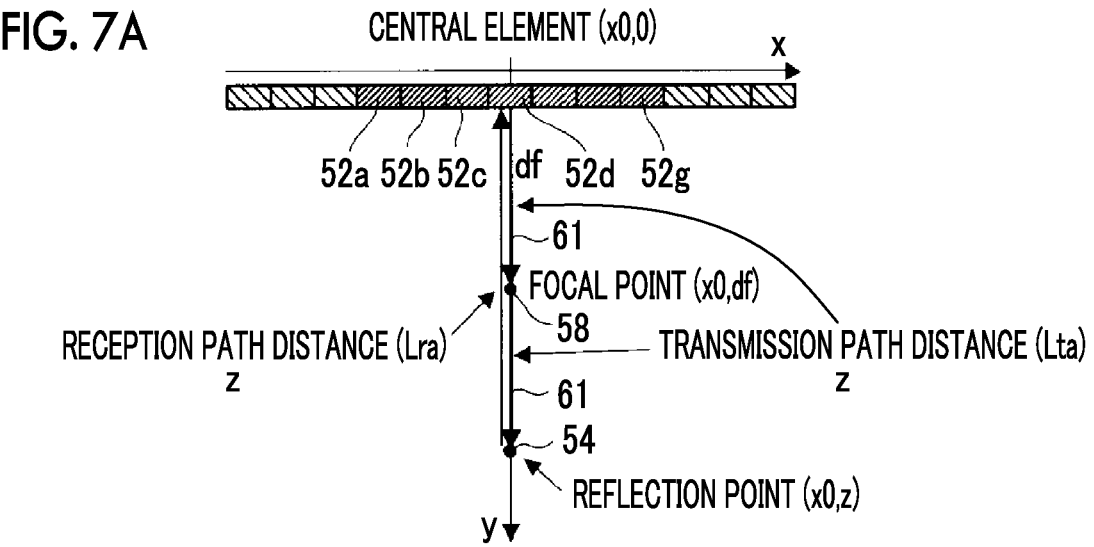
FIGS. 7A and 7B are conceptual diagrams illustrating a path of sonic waves in a case where transmission and reception of ultrasonic waves by different central elements are performed for the same reflection point.
Figure 7B:
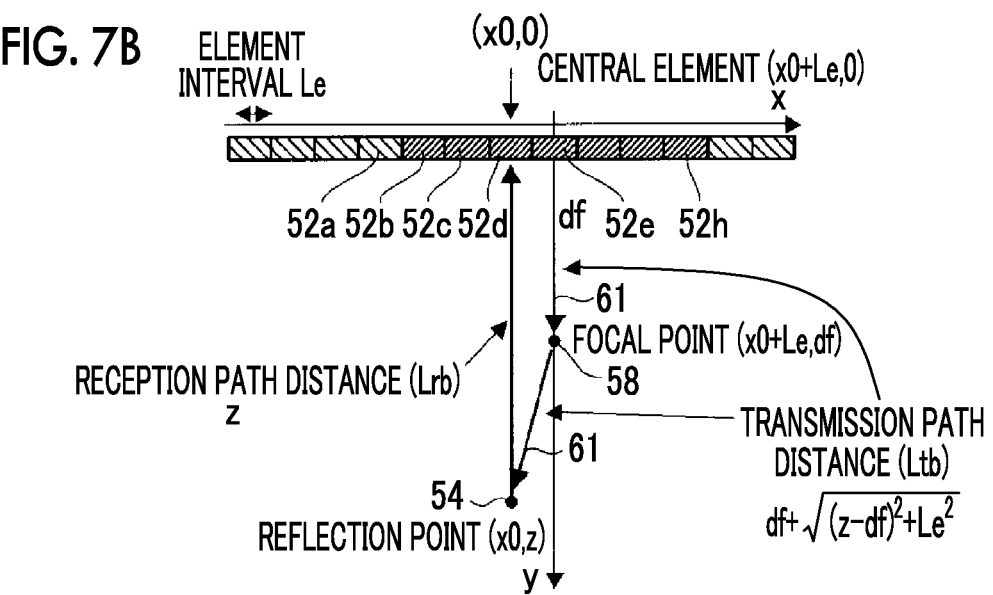

In the invention, for example, as shown in FIGS. 7A and 7B, it is possible to determine the length of the transmission path and the reception path of the ultrasound beam in cases of the true ultrasonic echo and the reflection echo of ghost. In FIGS. 7A and 7B, the x direction is an azimuth direction, and the y direction is a depth direction.

FIG. 7A shows the same transmission and reception of an ultrasonic wave as in FIG. 6A, and FIG. 7B shows the same transmission and reception of an ultrasonic wave as in FIG. 6C.

In a case of the true ultrasonic echo, as shown in FIG. 7A (FIG. 6A), the element 52d as a central element, the focal point 58, and the reflection point 54 are positioned on a straight line (the positions in the azimuth direction match one another). That is, the focal point 58 and the reflection point 54 are positioned directly below the central element 52d.

Accordingly, if the position of the element 52d as a central element is set to the coordinates (x0,0) on two-dimensional coordinates of x-y, the x coordinates of the focal point 58 and the reflection point 54 become "x0". Hereinafter, the position of the focal point 58 in the transmission is set to the coordinates (x0,df), the position of the reflection point 54 is set to the coordinates (x0,z), and the element interval is referred to as Le.

At this time, the length (transmission path distance) Lta of a transmission path 61 of the ultrasound beam reaching the reflection point 54 from the element 52d as a central element through the focal point 58 and the length (reception path distance) Lra of a reception path 60 of the true reflection ultrasonic echo reaching the element 52d from the reflection point 54 can be calculated by Lta=Lra=z.

Accordingly, in a case of the true ultrasonic echo, a propagation distance Lua of the ultrasonic echo becomes Lua=Lta+Lra=2z.

Next, as shown in FIG. 7B, the transmission elements and the reception elements are shifted for one element in the x direction (azimuth direction) (shifted in the right direction of the drawing), and transmission and reception are performed with the element 52e as a central element. As shown in FIG. 6C, in this case, the reflection echo of ghost is reflected from the reflection point 54.

The reflection point 54 is positioned directly below the element 52d (the same position in the azimuth direction). Accordingly, as shown in FIG. 7B, in the transmission and reception, the positions of the element 52e as a central element and the reflection point 54 in the x direction are shifted in the x direction for one element, that is, by Le.

Since the coordinates of the element 52d whose position in the x direction matches the reflection point 54 are (x0,0), the coordinates of the element 52e as a central element become (x0+Le,0), and the coordinates of the focal point 58 in the transmission become (x0+Le,df). As described above, the coordinates of the reflection point 54 are (x0,z).

Accordingly, the length (transmission path distance) Ltb of the transmission path 61 of the ultrasound beam reaching the reflection point 54 from the element 52e as a central element through the focal point 58 can be calculated by $Ltb = df + \sqrt{(z-df)^2 + Le^2}$. The length (reception path distance) Lrb of the reception path 60 of the reflection signal of ghost reaching the element 52d directly below the reflection point 54 (the same position in the x direction=the azimuth direction) from the reflection point 54 can be calculated by Lrb=z.

Accordingly, in a case of the reflection echo of ghost, the propagation distance Lub of the ultrasonic wave becomes $Lub = Ltb + Lrb = df + \sqrt{(z-df)^2 + Le^2} + z$.

In this way, a value obtained by dividing the propagation distance Lua of the ultrasonic wave as the sum of the distance Lta of the transmission path 61 and the distance Lra of the reception path 60 determined from the geometrical arrangement shown in FIG. 7A by the sound speed becomes the propagation time of the true ultrasonic echo. A value obtained by dividing the propagation distance Lub of the ultrasonic wave as the sum of the distance Ltb of the transmission path 61 and the distance Lrb of the reception path 60 determined from the geometrical arrangement shown in FIG. 7B by the sound speed becomes the propagation time of the reflection echo of ghost.

The delay time is determined from the difference between the propagation time of the true ultrasonic echo when the x coordinates of the reflection point 54 and the central element match each other and the propagation time of the reflection echo of ghost when the x coordinates of the reflection point 54 and the central element are shifted by one element interval.

In the geometrical models of FIGS. 7A and 7B, although a model in which the transmission path 61 passes through the focal point 58 has been shown, the invention is not limited thereto, and for example, the transmission path may be a path which directly reaches the reflection point 54 without passing through the focal point 58.

Although the geometrical models of FIGS. 7A and 7B are applied to a linear probe, the invention is not limited thereto, in other probes, the same geometrical calculation can be performed from the shape of the probe.

For example, in a case of a convex probe, a geometrical model can be set from the radius of the probe and the angle of the element interval, and the same calculation can be performed.

In a case of steering transmission, a geometrical model in consideration of information relating to a transmission angle and the like can be used, and the delay time of true element data and the delay time of element data of peripheral ghost can be calculated from the positional relationship between the transmission element and the reflection point.

The invention is not limited to the calculation method of the delay time using the geometrical model, and a delay time may be determined for each measurement condition from a measurement result of measuring a high-luminance reflection point according to the measurement conditions of the device in advance, the delay time may be stored in the device, and the delay time of the same measurement condition may be read.

Figure 7C:
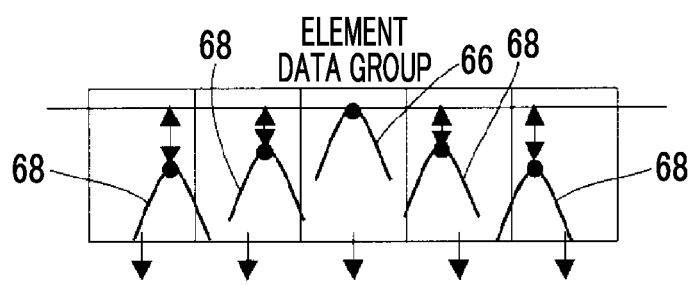
FIG. 7C is a conceptual diagram of element data obtained by a plurality of elements.

FIG. 7C shows true element data 66 and element data 68 of ghost.

In FIG. 7C, the center in the azimuth direction is true element data 66, that is, element data (in the example of the drawing, element data with the element 52d as a central element) obtained by transmission and reception in which the positions of the central element and the reflection point 54 in the x direction match each other. Both sides of the center are element data of ghost, that is, element data (in the example of the drawing, element data with the element 52c, the element 52e, or the like as a central element) obtained by transmission and reception in which the positions of the central element and the reflection point 54 in the x direction do not match each other.

Figure 7D:
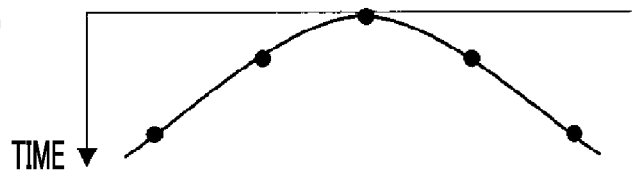
FIG. 7D is a conceptual diagram illustrating a delay time of element data shown in FIG. 7C.

FIG. 7D shows an example of the delay time of element data 68 with respect to true element data 66 obtained from the above-described geometrical calculation. True element data 66 is at the center, and element data 68 of the ghost signal is delayed symmetrically in the x direction, that is, in the azimuth direction.

In this way, the delay time calculated in the delay time calculation unit 48 of the element data processing unit 35 may be used for delay correction in the phasing addition unit 38.

Though described below in detail, in the invention, element data obtained by transmission of an ultrasonic beam, for which the central element is different and at least a part of the ultrasound beam overlaps, is superimposed on element data obtained by transmission with a certain element of interest as a central element (transmission and reception of an element of interest) according to the reception time of the ultrasonic echo and the position of the element to generate processed element data (second element data) of the element of interest (to reconstruct element data of the element of interest).

In FIG. 7A, the reflection point 54 indicates the position (the output position of element data) of a certain sampling point directly below the element of interest (on the same position in the azimuth direction/a straight line connecting the element of interest and the focal point). In the invention, the transmission and reception path to the sampling point in the transmission and reception of the element of interest is regarded as the transmission and reception path of true element data, the transmission and reception path to the same sampling point in transmission and reception of an ultrasonic wave with a different central element (transmission and reception from a peripheral element) is regarded as the transmission and reception path of ghost, the delay time is calculated from the difference between both transmission paths, and superimposition is performed using the delay time according to the time of element data. In other words, on an assumption that element data obtained by transmission and reception of the element of interest is true element data and element data obtained by transmission and reception with a different central element is element data of ghost, the delay time is calculated and superimposition of element data is performed.

In the invention, the delay time is calculated by the same way of thinking corresponding to all sampling points (all output positions of element data), and superimposition of element data is performed to generate processed element data of the respective elements.

Actually, even if the position of the sampling point (reflection point) is shifted in the azimuth direction (x direction), the length (reception path distance Lrb) of the reception path is not changed. Accordingly, in regard to each element of interest, the calculation of the delay time from element data by transmission and reception with a different central element may be performed for each sampling point in the depth direction (y direction).

In the superimposition processing, it is not necessary to know which element data is true element data. That is, though described below in detail referring to parts (a) to (h) of FIG. 8, in the superimposition processing, if a signal included in element data is a true signal, the signal is automatically enhanced and remains, and if a signal included in element data is a ghost signal, the signal is canceled. That is, if the reflection point exists on the line of the element of interest, a signal from the reflection point is enhanced by matching the processing depending on the delay time. In regard to a signal from the reflection point on a line other than the element of interest, the signal is canceled without matching the processing depending on the delay time.

Next, in the superimposition processing unit 49 of the element data processing unit 35 of the invention, the superimposition processing of element data is performed using the delay time calculated in the delay time calculation unit 48 in this way.

In the superimposition processing in the superimposition processing unit 49, although information relating to the number of pieces of element data to be superimposed and the superimposition processing method at the time of superimposition is required, these kinds of information may be input by the operating unit 32 or stored in the storage unit 34 in advance.

Parts (a) to (h) of FIG. 8 show an example of the superimposition processing which is performed in the superimposition processing unit 49. In the example shown in parts (a) and (h) of FIG. 8, the number of pieces of element data is five, and the number of pieces of element data to be superimposed is three.

Part (a) of FIG. 8 shows five pieces of element data obtained by transmission and reception of an ultrasonic wave five times in parallel in a horizontal direction. Part (a) of FIG. 8 shows a manner in which an ultrasound beam is transmitted and an ultrasonic echo is received for each piece of element data. The horizontal axis of each piece of element data represents reception elements, and the reception elements are shown centering on the central element in the transmission and reception of the ultrasound beam in each piece of element data. The vertical axis represents a reception time. In this example, for example, the central element, such as the elements 52b to 52f, is shifted by one element, and transmission and reception of the ultrasonic wave are performed five times.

Part (a) of FIG. 8 shows a state where one reflection point exists only directly below the central element in central element data. That is, in middle element data among five pieces of element data, the true ultrasonic echo from the reflection point is received in the transmission and reception of the ultrasonic wave. That is, middle element data is true element data.

In regards to two pieces of element data on both sides other than middle element data, the reflection point does not exist directly below the central element in the transmission and reception of the ultrasonic wave. However, element data of the reflection echo generated when the ultrasound beam hits the reflection point existing directly below the transmission element of middle element data due to the spread of the transmitted ultrasound beam, that is, element data of ghost is projected.

When element data of ghost is separated farther away from true element data, the propagation time of the ultrasonic wave to the reflection point becomes longer; thus, the reception time of element data of ghost is delayed compared to that of true element data. The reception element where the ultrasonic echo from the reflection point is first received is an element (an element whose position in the azimuth direction matches the reflection point) directly above the reflection point.

The horizontal axis of each piece of element data of part (a) of FIG. 8 centers on the central element at the time of transmission of the ultrasound beam. Accordingly, in the example shown in part (a) of FIG. 8, each piece of element data is transmitted while shifting the central element by one element; thus, the absolute position of the element in the azimuth direction in each piece of element data is shifted by one element. That is, in middle element data, the reception element where the reflection signal from the reflection point is first received is the central element; however, in element data on both sides, the central element is shifted by one element compared to middle element data, specifically, in element data on the right side, the central element is shifted to the left by one element, and in element data on the left side, the central element is shifted to the right by one element. In element data on both adjacent sides, the central elements is shifted by two elements compared to middle element data, specifically, in element data at the right end, the central element is shifted to the left by two elements, and in element data at the left end, the central element is shifted to the right by two elements. In this way, not only the reception time of the ghost signal is delayed with respect to the true signal, and but also shift occurs with respect to the direction of the reception elements.

Part (b) of FIG. 8 shows an example of the delay time of the reception time with respect to middle element data among the five pieces of element data shown in part (a) of FIG. 8.

In the superimposition processing unit 49, using the delay time shown in part (b) of FIG. 8, in a case where the central element of middle element data is used as an element of interest, delay time correction is performed by the number of pieces of element data to be superimposed centering on element data of the element of interest, in the example of the drawing, by three pieces of element data, and unprocessed element data for three pieces of element data are superimposed while shifting each piece of element data, in the example of the drawing, each piece of element data on both sides in the azimuth direction by one element according to the difference in element position from the element of interest (the difference in position between the central elements), that is, while adjusting the phase, and determined as one piece of superimposition-processed element data of the element of interest.

That is, in this example, element data (hereinafter, referred to as element data of the adjacent element) obtained by transmission and reception of the ultrasonic wave with the element adjacent to the element of interest as the central element is superimposed on element data (hereinafter, referred to as element data of the element of interest) by transmission and reception of the ultrasonic wave with the element of interest as the central element to generate processed element data of element data of the element of interest.

Superimposition-processed element data of the element of interest obtained in this way is shown in part (c) of FIG. 8.

As described above, element data of the element of interest shown in part (a) of FIG. 8 is true element data in which the reflection point exists directly below the central element (that is, the element of interest). Element data obtained by transmission and reception with the element adjacent to the element of interest as the central element is also data of the ultrasonic echo which enters the reflection point and is reflected from the reflection point.

Accordingly, if phase matching is performed by performing the delay time correction and the shift in the azimuth direction on element data of the adjacent elements on both sides of element data of the element of interest, as shown in part (c) of FIG. 8, element data of the adjacent elements and element data of the element of interest are superimposed at a high-luminance position since the phases match each other. For this reason, if these pieces of element data are added, the element data value indicates a large value (high-luminance value), and for example, even if an average value is determined by averaging the pieces of element data, the average value indicates an enhanced value (high-luminance value).

In contrast, part (d) of FIG. 8 shows an example of a case where the central element of element data which is the same element data at that shown in part (a) of FIG. 8 but is on the left of middle element data is used as the element of interest. That is, this example shows an example of a case where a central element in transmission and reception of an ultrasonic wave with an element with no reflection point directly there below as a central element is used as an element of interest. Accordingly, element data with this element as the central element is element data of ghost.

Superimposition-processed element data of the element of interest obtained in this way is shown in part (f) of FIG. 8.

Element data of the element of interest shown in part (d) of FIG. 8 is element data of ghost. For this reason, even if phase matching is performed by performing the delay time correction and the shift in the azimuth direction on unprocessed element data of adjacent elements on both sides of element data of the element of interest, as shown in part (f) of FIG. 8, each piece of element data of the adjacent elements and element data of the element of interest are not superimposed since the phases do not match each other. For this reason, even if the three pieces of element data are added, since the phases do not match each other, and signals having inverted phases are canceled, the sum value is not increased, and for example, if an average value is determined by averaging the pieces of element data, the average value indicates a small value.

As a result of performing the delay time correction and the shift in the azimuth direction on other pieces of element data as element data of the element of interest, a superimposition state of three pieces of element data on each of five pieces of element data in the example of the drawing is shown in part (g) of FIG. 8, and a result of performing addition processing or average processing as superimposition processing on these pieces of element data is shown in part (h) of FIG. 8.

As shown in part (h) of FIG. 8, in a case where the central element shown in part (a) of FIG. 8 with the reflection point directly there below is used as the element of interest, element data of the true signal is determined as superimposition-processed element data having a high-luminance value. In contrast, in four pieces of element data in total including two pieces of element data on both sides, pieces of element data of ghost where the phases do not match each other are added or averaged. For this reason, since the pieces of element data are canceled each other, superimposition-processed element data of ghost is smaller than superimposition-processed element data having a high-luminance value as element data of the true signal, and it is possible to reduce the influence of element data of ghost with respect to true element data and to minimize element data of ghost such that the influence is negligible.

That is, processed element data corresponding to element data of the element of interest is generated by superimposing one or more pieces of element data obtained by transmission and reception of the ultrasonic wave, for which the central element is different and the transmission region of the ultrasound beam overlaps, on element data (element data of the element of interest) obtained by transmission of the ultrasound beam, for which a certain element is used as an element of interest and the element of interest is used as the central element, while performing time and azimuth direction positioning (in other words, by reconstructing (correcting) element data of the element of interest using element data obtained by transmission and reception where at least a part of the ultrasound beam overlaps and the central element is different), whereby it is possible to make true element data have high luminance and to reduce element data of ghost.

For this reason, since it is possible to generate the B mode image with element data such that the influence of ghost is eliminated, that is, the focal points at all points on the sound ray are connected by performing phasing addition or detection processing on processed element data to generate reception data, and generating the B mode image, it is possible to generate a high-image quality B mode image with high luminance and excellent sharpness.

In the following description, the generation of processed element data is also referred to as multiline processing.

Processed element data is one of processed data in the invention.

In the invention, the central element is an element at the center in the azimuth direction in a case where the number of transmission openings (the number of elements which perform transmission of an ultrasonic wave) is an odd number.

Meanwhile, in a case where the number of openings is an even number, any one of the elements at the center in the azimuth direction is used as the central element, or assuming that there is an element in the middle of the azimuth direction, the element is used as the central element. That is, in a case where the number of openings is an even number, the calculation may be performed by providing a focal point on a line in the middle of the opening.

As the superimposition processing method in the superimposition processing unit 49, an average value or a median value may be taken instead of only adding, or addition may be performed after multiplication with a coefficient. Taking the average value or the median value may be considered equivalent to applying an averaging filter or a median filter at an element data level; however, an inverse filter or the like which performs normal image processing may be applied instead of the averaging filter or the median filter.

Alternatively, the pieces of element data to be superimposed are compared, a maximum value is taken in a case where the pieces of element data are not similar, an average value is taken in a case where the pieces of element data are similar, and an intermediate value is taken in a case where th distribution is biased; however, the invention is not limited thereto, and the superimposition processing may be changed based on the feature amount of each piece of element data to be superimposed.

The number of pieces of element data to be superimposed on element data of the element of interest is not limited to two in the example of the drawing, and may be one, or three or more. That is, the number of pieces of element data to be superimposed on element data of the element of interest may be appropriately set according to a required processing rate (frame rate or the like), image quality, or the like. Basically, when the number of element data to be superimposed is larger, image quality is further improved.

It is preferable that the number of pieces of element data to be superimposed on element data of the element of interest matches the extent of the spread of the beam width of the ultrasound beam. Accordingly, in a case where the beam width changes according to the depth, the number of pieces of element data to be superimposed may be changed according to the depth.

Since the beam width depends on the number of transmission openings, the number of pieces of element data to be superimposed may be changed according to the number of transmission openings. Alternatively, the number of pieces of element data to be superimposed may be changed based on the feature amount, such as the luminance value of the image, or the optimum number of pieces of element data to be superimposed may be selected from an image created by changing the number of pieces of superimposed element data into a plurality of patterns.

In the above multiline processing, although processed element data of element data of the element of interest is generated by superimposing element data obtained by transmission of a plurality of ultrasound beams, for which the central elements are different and the transmission directions of the ultrasound beams are parallel (the angles are the same), the invention is not limited thereto.

For example, processed element data may be generated by superimposing element data obtained by transmission of a plurality of ultrasound beams where the central elements are the same and the transmission directions (angles) are different. At this time, whether to generate processed element data of element data obtained by transmission of any ultrasound beam (that is, whether to generate processed element data of a sound ray in any direction) may be set by default according to a diagnosis region, the type of probe, or the like, or may be selected by the operator.

Processed element data may be generated using both of element data obtained by transmission where the central elements are different and the ultrasound beams are parallel and element data obtained by transmission where the central elements are the same and the transmission directions of the ultrasound beams are different.

As described above, the element data processing unit 35 sends the generated processed element data to the image generation unit 37 (phasing addition unit 38).

In the image generation unit 37 to which processed element data is supplied, as described above, the phasing addition unit 38 performs reception focusing processing by performing phasing addition on processed element data to generate reception data, and the detection processing unit 40 performs attenuation correction and envelope detection processing on reception data to generate B mode image data.

In addition, in the image generation unit 37, the DSC 42 raster-converts the B mode image data to image data corresponding to a typical television signal scan system, and predetermined processing, such as gradation processing, is performed in the image processing unit 44.

The image processing unit 44 stores the generated B mode image data in the image memory 46 and/or sends the generated B mode image data to the display image generation unit 25.

As described above, in a case where the display mode is the color mode, the processing region setting unit 47 sets a processing region based on information relating to the color region ROI set in the region setting unit 21, and the superimposition processing unit 49 performs multiline processing in the set processing region.

Specifically, the processing region setting unit 47 sets a region including at least a line passing through the color region ROI as the processing region.

An example of a setting method of a processing region in the processing region setting unit 47 will be described in detail referring to FIGS. 9A and 9B.

FIG. 9A is a conceptual diagram illustrating the relationship between a color region ROI and a processing region set in an imaging region. In the drawing, the horizontal direction corresponds to the arrangement direction of the elements, and the vertical direction corresponds to the depth direction.

As shown in FIG. 9A, if the color region ROI indicated using a solid line is set in the imaging region, the processing region setting unit 47 sets a range (in the drawing, a range indicated using broken lines) including a line passing through the color region ROI as a processing region.

If the processing region is set, the superimposition processing unit 49 performs multiline processing on element data corresponding to the line in the processing region to generate processed element data corresponding to each line of the processing region and does not perform multiline processing on element data corresponding to lines in other regions. That is, a B mode image of the processing region is generated from processed element data generated through the multiline processing, and a B mode image of a region other than the processing region is generated from unprocessed element data.

As described above, the multiline processing is performed when generating the B mode image, whereby it is possible to improve image quality without influence of the ghost signal. However, if the multiline processing is performed on the lines in the entire imaging region, a calculation load is increased and a long processing time is required. When generating a color Doppler image, in order to secure sensitivity when detecting a Doppler effect and to improve image quality, it is necessary to increase the number of transmission in the same direction.

For this reason, in the color mode in which the B mode image and the color Doppler image are displayed in a superimposed manner, if the multiline processing is performed when generating the B mode image, there is a problem in that the frame rate is significantly degraded and real time performance is damaged.

In contrast, in the invention, in the color mode, when generating the B mode image, the processing region setting unit 47 sets the processing region for the multiline processing based on information relating to the color region ROI as a region where the color Doppler image is generated, and the superimposition processing unit 49 performs the multiline processing on element data corresponding to the line in the set processing region to generate processed element data and does not perform the multiline processing on element data corresponding to the lines outside the processing region. The image generation unit 37 generates the B mode image corresponding to the processing region from processed element data and generates the B mode image of the region other than the processing region from unprocessed element data.

In this way, the range in which the multiline processing is performed is restricted, whereby it is possible to reduce a calculation load due to the multiline processing while improving image quality of the B mode image of the region corresponding to the color region ROI deemed as being noticed by the operator, to prevent degradation of the frame rate, and to secure real time performance of display in the color mode.

In the example shown in FIG. 9A, although the shape of the color region ROI is a rectangular shape, and the transmission and reception direction of the ultrasonic wave for generating the B mode image and the transmission and reception direction of the ultrasonic wave for generating the color Doppler image match each other, the invention is not limited thereto. That is, the transmission and reception direction of the ultrasonic wave for generating the B mode image and the transmission and reception direction of the ultrasonic wave for generating the color Doppler image may be different from each other.

FIG. 9B is a conceptual diagram illustrating the relationship between a color region ROI and a processing region set in an imaging region. In the drawing, the horizontal direction corresponds to the arrangement direction of the elements, and the vertical direction corresponds to the depth direction.

As shown using a solid line in FIG. 9B, the color region ROI is set as a region inclined with respect to the arrangement direction of the elements in the depth direction. That is, the color Doppler image of the color region is generated by transmission and reception of an ultrasonic wave steering-transmitted in a direction inclined in the depth direction.

The transmission and reception direction of the ultrasonic wave for generating the B mode image superimposed on the color Doppler image is a direction orthogonal to the arrangement direction of the elements. That is, the transmission and reception direction of the ultrasonic wave for generating the B mode image does not match the transmission and reception direction of the ultrasonic wave for generating the color Doppler image.

In this case, the processing region setting unit 47 sets, as a processing region, a region including a line passing through the color region ROI indicated by broken lines in the drawing among the lines for transmitting and receiving the ultrasonic wave for generating the B mode image are performed.

Even in a case where the processing region is set in this way, it is possible to reduce a calculation load due to the multiline processing while improving image quality of the B mode image of the region corresponding to the color region ROI, to prevent degradation of the frame rate, and to secure real time performance of display in the color mode.

In the example of the drawing, although the processing region setting unit 47 sets the region including the line passing through the color region ROI as the processing region, the invention is not limited thereto, and a region including a sampling point in the color region ROI may be set as a processing region.

While the setting operation of the color region ROI is performed in the operating unit 32, the processing region setting unit 47 may set the processing region to be none. That is, while the operator performs an operation to set the color region ROI, it can be deemed that an image is not always observed in detail in order to perform diagnosis; thus, while the setting operation of the color region ROI is performed, the processing region is set to be none, and the multiline processing is not performed, thereby maintaining a high frame rate.

Hereinafter, a signal processing method (a signal processing method of the invention) in the ultrasound diagnostic apparatus 10 will be described in detail referring to the flowchart shown in FIG. 10.

A program of the invention is a program which causes a computer in the ultrasound diagnostic apparatus 10 to execute the following signal processing method.

In the ultrasound diagnostic apparatus 10, if the color mode is selected, first, display for prompting a setting of the color region ROI is performed, and the region setting unit 21 sets the color region ROI according to an input instruction from the operator using the operating unit 32. If the color region ROI is set, in order to generate the color Doppler image in the Doppler processing unit 22, the transmission unit 14 transmits the ultrasound beam to the subject by driving (with a predetermined number of openings and the positions of the openings) the corresponding ultrasound transducers (elements) of the probe 12 (transducer array 36) in response to an instruction from the control unit 30, the ultrasonic echoes reflected from the subject are received by the ultrasound transducers (elements), and analog reception signals are output to the reception unit 16.

The reception unit 16 performs predetermined processing, such as amplification, on the analog reception signals, and supplies the analog reception signals to the A/D conversion unit 18.

The A/D conversion unit 18 A/D converts the analog reception signals supplied from the reception unit 16 to element data as digital reception signals.

Element data is stored in the element data storage unit 20.

The Doppler processing unit 22 sequentially reads element data stored in the element data storage unit 20, performs frequency analysis of element data to generate Doppler data representing a relative moving speed of the subject and the ultrasound probe 12, converts Doppler data to color information using a speed conversion scale designated in advance, and performs predetermined processing on the color information to generate color Doppler image data. The Doppler processing unit 22 supplies the generated color Doppler image data to the display image generation unit 25.

Next, in order to generate the B mode image in the B mode processing unit 24, first, the processing region setting unit 47 sets the processing region based on the color region ROI. The transmission unit 14 transmits the ultrasound beam to the subject by driving the corresponding elements of the probe 12 in response to an instruction from the control unit 30, the ultrasonic echoes reflected from the control unit 30 are received by the ultrasound transducers, and analog reception signals are output to the reception unit 16.

The reception unit 16 performs predetermined processing, such as amplification, on the analog reception signals and supplies the analog reception signals to the A/D conversion unit 18, and the A/D conversion unit 18 A/D converts the analog reception signals supplied from the reception unit 16 to element data as digital reception signals.

Element data is stored in the element data storage unit 20.

In regard to element data corresponding to the line in the processing region set by the processing region setting unit 47, the element data processing unit 35 reads element data stored in the element data storage unit 20 and performs the multiline processing on the read element data to generate processed element data.

Specifically, as shown in parts (a) to (h) of FIG. 8 described above, for example, the element data processing unit 35 calculates the delay time of element data of both adjacent elements with respect to element data of the element of interest for the element of interest and both adjacent elements, performs the delay time correction and the shift in the azimuth direction on element data of the adjacent elements, and superimposes element data of both adjacent elements on element data of the element of interest to generate processed element data of the element of interest.

The element data processing unit 35 performs superimposition of element data on each piece of element data corresponding to the lines in the processing region to generate a plurality of pieces of processed element data. The element data processing unit 35 supplies the generated processed element data to the image generation unit 37. The image generation unit 37 generates B mode image data using processed element data and unprocessed element data corresponding to the lines of the region other than the processing region. The generated B mode image data is supplied to the display image generation unit 25.

The display image generation unit 25 synthesizes the supplied color Doppler image data and B mode image data to generate synthesized image data and supplies synthesized image data to the display control unit 26. The display control unit 26 displays the supplied synthesized image (ultrasound image) on the display unit.

In this way, in the color mode, when generating the B mode image, the multiline processing is performed only on element data corresponding to the lines in the processing region set based on the color region ROI; thus, it is possible to reduce a calculation load due to the multiline processing while improving image quality of the B mode image of the region corresponding to the color region ROI, to prevent degradation of the frame rate, and to secure real time performance of display in the color mode.

In a case where the color mode is not selected, for example, in a case where the B mode is selected, as shown in FIG. 10, first, element data is acquired by performing transmission and reception of an ultrasonic wave under the control of the control unit 30. Next, a B mode image is generated in the B mode processing unit 24. At this time, the element data processing unit 35 performs the multiline processing on element data corresponding to all lines in the imaging region to generate processed element data. The element data processing unit 35 supplies the generated processed element data to the image generation unit 37, and the image generation unit 37 generates B mode image data using processed element data. The generated B mode image data is supplied to the display control unit 26 for display.

In the first embodiment, although a configuration in which the multiline processing is performed only on element data corresponding to the lines in the processing region has been made, the invention is not limited thereto, and a configuration in which multiline processing is performed on element data corresponding to the lines of the region other than the processing region with superimposition a smaller number of times than the multiline processing on element data corresponding to the lines in the processing region may be made.

In the first embodiment, although a configuration in which the multiline processing in the element data processing unit 35 is performed using element data has been made, the invention is not limited thereto, and a configuration in which multiline processing is performed on first reception data obtained by performing phasing addition on first element data may be made.

FIG. 11 conceptually shows an example of a B mode processing unit of an ultrasound diagnostic apparatus according to a second embodiment of the invention using a block diagram.

The ultrasound diagnostic apparatus of the second embodiment has the same configuration as the ultrasound diagnostic apparatus 10 shown in FIG. 1, except that a B mode processing unit 112 is provided instead of the B mode processing unit 24.

The B mode processing unit 112 shown in FIG. 11 has the same configuration as the B mode processing unit 24 shown in FIG. 2, except that a data processing unit 114 is provided instead of the element data processing unit 35 and an image generation unit 116 is provided instead of the image generation unit 37; thus, the same components are represented by the same reference numerals, and detailed description thereof will not be repeated.

The B mode processing unit 112 is a unit which generates a B mode image from element data stored in the element data storage unit 20, and has a data processing unit 114 and an image generation unit 116.

FIG. 12 conceptually shows the configuration of the data processing unit 114 using a block diagram.

The data processing unit 114 has a phasing addition unit 118, a processing region setting unit 47, a delay time calculation unit 48, and a superimposition processing unit 120.

The phasing addition unit 118 performs reception focusing processing by performing phasing addition on element data read from the element data storage unit 20 to generate first reception data (unprocessed reception data).

The phasing addition unit 118 performs the reception focusing processing on one piece of element data multiple times while changing a reference line, and generates two or more pieces of unprocessed reception data for each piece of element data.

The superimposition processing unit 120 acquires unprocessed reception data generated in the phasing addition unit 118 based on information relating to data processing, such as the number of pieces of data to be superimposed and the superimposition processing method.

The superimposition processing unit 120 superimposes two or more pieces of unprocessed reception data based on the delay time corresponding to each piece of unprocessed reception data calculated by the delay time calculation unit 48 on the reception time, that is, according to the time to generate processed (second) reception data.

Specifically, the superimposition processing unit 120 superimposes unprocessed reception data obtained by performing phasing addition processing on unprocessed reception data supplied from the phasing addition unit 118 in the same line according to the reception time of the ultrasonic echo of each ultrasound transducer to generate processed reception data corresponding to one piece of unprocessed reception data.

Processed reception data is one of processed data of the invention.

The phasing addition unit 118 and the superimposition processing unit 120 will be described in more detail referring to parts (a) to (i) of FIG. 13 and (a) to (h) of FIG. 14.

First, the phasing addition processing in the phasing addition unit 118 will be described in detail referring to parts (a) to (i) of FIG. 13.

Parts (a), (d), and (g) of FIG. 13 are conceptual diagrams illustrating respective reception elements, parts (b), (e), and (h) of FIG. 13 are conceptual diagrams showing element data obtained by transmission and reception of ultrasonic waves, and parts (c), (f), and (i) of FIG. 13 are conceptual diagrams showing unprocessed reception data obtained by performing phasing addition processing on respective pieces of element data.

Parts (a) to (i) of FIG. 13 show a state where a reflection point exists on a line corresponding to an n-th element.

First, an example where two or more pieces of unprocessed reception data are generated from one piece of element data will be described referring to parts (a) to (c) of FIG. 13.

Part (a) of FIG. 13 is a diagram conceptually showing the transducer array 36 having a plurality of elements arranged. In part (a) of FIG. 13, the position of the element is represented using n, and reception elements are hatched. That is, part (a) of FIG. 13 shows that (n−4)th to (n+4)th elements are reception elements with the n-th element as a central element.

Part (b) of FIG. 13 is a diagram conceptually showing element data acquired by reception element shown in part (a) of FIG. 13 The position of part (b) of FIG. 13 is displayed corresponding to the position of reception element shown in part (a) of FIG. 13.

In the following description, the element data obtained using the n-th element as a central element is referred to as n-th element data.

The phasing addition unit 118 reads n-th element data from the element data storage unit 20 and performs the phasing addition processing with a line (hereinafter, referred to as an n-th line) corresponding to the n-th element as a reference line to generate n(n)-th unprocessed reception data shown at the center of part (c) of FIG. 13. The phasing addition unit 118 performs the phasing addition processing on n-th element data with an (n−2)th line as a reference line to generate n(n−2)th unprocessed reception data shown on the left of part (c) of FIG. 13. Similarly, the phasing addition processing is performed on n-th element data with (n−1)th, (n+1)th, and (n+2)th lines as a reference line to generate n(n−1)th unprocessed reception data, n(n+1)th unprocessed reception data, and n(n+2)th unprocessed reception data.

In this specification, for example, reception data generated by performing phasing addition on x-th element data with a y-th line as a reference is represented as x(y)-th reception data.

That is, the phasing addition unit 118 of this embodiment performs the phasing addition processing on one piece of element data using five lines in total including the line corresponding to the central element of the reception element corresponding to element data and the lines corresponding to the respective two elements on the right and left of the central element to generate five pieces of unprocessed reception data as shown in part (c) of FIG. 13.

Accordingly, as shown in parts (d) to (f) of FIG. 13, the phasing addition processing is performed on (n−1)th element data using (n−3)th to (n+1)th lines centering on the (n−1)th line to generate five pieces of unprocessed reception data shown in part (f) of FIG. 13. As shown in parts (g) to (i) of FIG. 13, the phasing addition processing is performed on (n+1)th element data using (n−1)th to (n+3)th lines centering on the (n+1)th line to generate five pieces of unprocessed reception data shown in part (i) of FIG. 13.

In this way, the phasing addition unit 118 performs the phasing addition processing on necessary element data multiple times to generate a plurality of pieces of unprocessed reception data.

The phasing addition unit 118 supplies unprocessed reception data to the superimposition processing unit 120.

In the phasing addition unit 118, the number of pieces of unprocessed reception data generated from one piece of element data is not particularly limited, and may be appropriately determined according to the performance of the device, a required processing rate (frame rate or the like), image quality, and the like.

It is preferable that the phasing addition unit 118 generates, according to the width of the ultrasound beam, unprocessed reception data for the lines corresponding to the width. With this, it is possible to sufficiently exhibit the effect of superimposition and to reduce the amount of data to be stored. The width of the ultrasound beam is the width of the ultrasound beam at the depth of the sampling point.

Specifically, it is preferable that the phasing addition unit 118 generates unprocessed reception data for three to ten lines from one piece of element data.

The line for performing the phasing addition processing is not particularly limited; however, it is preferable that the phasing addition processing is performed with the line of the central element of the reception element corresponding to element data and the lines of two or more adjacent elements on the right and left of the central element for each piece of element data.

Next, the superimposition processing in the superimposition processing unit 120 will be described in detail referring to Parts (a) to (h) of FIG. 14.

Parts (a) and (e) of FIG. 14 are conceptual diagrams showing unprocessed reception data to be superimposed, parts (e) and (f) of FIG. 14 are conceptual diagrams illustrating the delay time of each piece of unprocessed reception data, parts (c) and (g) of FIG. 14 are conceptual diagrams illustrating a state of superimposition of unprocessed reception data, and parts (d) and (h) of FIG. 14 are conceptual diagrams illustrating a result of superimposition of unprocessed reception data.

An example shown in parts (a) to (h) of FIG. 14 is an example where the number of times of superimposition in the superimposition processing unit 120 is five.

Unprocessed reception data shown in parts (a) and (e) of FIG. 14 are unprocessed reception data in a state where a reflection point exists on an n-th line.

As shown in part (a) of FIG. 14, in a case of generating processed reception data corresponding to n(n)th unprocessed reception data, the superimposition processing unit 120 acquires five pieces of unprocessed reception data (n−2(n), n−1(n)th, n(n)th, n+1(n)th, and n+2(n)th unprocessed reception data) which are unprocessed reception data generated by performing the phasing addition processing on different pieces of element data with the n-th line as a reference.

The superimposition processing unit 120 performs the delay time correction on the five pieces of unprocessed reception data based on the delay time (part (b) of FIG. 14) calculated by the delay time calculation unit 48, superimposes unprocessed reception data (part (c) of FIG. 14), and performs addition or averaging to generate processed reception data corresponding to n(n)th unprocessed reception data (part (d) of FIG. 14). The generated processed reception data is processed reception data corresponding to the n-th element (line).

In the color mode, the superimposition processing unit 120 performs superimposition processing on unprocessed reception data corresponding to the processing region set according to the color region ROI to generate processed reception data and does not perform the superimposition processing on unprocessed reception data corresponding to the region other than the processing region.

With this, it is possible to reduce a calculation load due to the multiline processing while improving image quality of the B mode image of the region corresponding to the color region ROI, to prevent degradation of the frame rate, and to secure real time performance of display in the color mode.

Similarly, in a case of generating processed reception data corresponding to the (n−1)th line, the superimposition processing unit 120 acquires five pieces of unprocessed reception data (part (e) of FIG. 14) generated by performing the phasing addition processing with the (n−1)th line as a reference.

The superimposition processing unit 120 performs the delay time correction on five pieces of unprocessed reception data based on the delay time (part (f) of FIG. 14), superimposes unprocessed reception data (part (g) of FIG. 14), and performs addition or averaging to generate (n−1)th processed reception data (part (h) of FIG. 14).

As in parts (a) to (d) of FIG. 14, if the delay time correction is performed on unprocessed element data subjected to the phasing addition processing with a line (n-th line) having the reflection point as a reference and superimposition is performed, the phases of the signals from the reflection point match each other; thus, the signals (true signals) from the reflection point indicate an enhanced value (high-luminance value) through the superimposition processing (part (d) of FIG. 14).

As in parts (e) to (h) of FIG. 14, even if the delay time correction is performed on unprocessed element data subjected to the phasing addition processing with a line ((n−1)th line) having no reflection point as a reference, the phases of the signals (ghost signals) from the reflection point do not match each other; thus, the signals are canceled each other and have a small value through superimposition (part (h) of FIG. 14).

In regards to other elements (lines), each element is used as an element of interest, and two or more pieces of unprocessed reception data subjected to the phasing addition processing with the line of the element of interest as a reference are read, and the superimposition processing is performed based on the delay time, whereby the true signals are enhanced and the ghost signals are canceled to reduce the influence of the ghost signals.

For this reason, since it is possible to generate the B mode image with reception data such that the influence of ghost is eliminated, that is, the focal points at all points on the sound ray are connected by performing detection processing or the like on processed reception data and generating the B mode image, it is possible to generate a high-image quality B mode image with high luminance and excellent sharpness.

In this way, the superimposition processing (multiline processing) may be performed using unprocessed reception data obtained by performing the phasing addition processing on element data. It is preferable that the superimposition processing is performed after the phasing addition processing is performed in that it is possible to reduce the amount of data to be held (stored).

The data processing unit 114 supplies the generated processed reception data to the image generation unit 116.

The image generation unit 116 has a detection processing unit 40, a DSC 42, an image processing unit 44, and an image memory 46.

In the image generation unit 116, the detection processing unit 40 performs attenuation correction and envelope detection processing on reception data to generate B mode image data. The DSC 42 raster-converts B mode image data to image data corresponding to a typical television scan system, and predetermined processing, such as gradation processing, is performed in the image processing unit 44.

The image processing unit 44 stores the generated B mode image data in the image memory 46 and/or sends the generated B mode image data to the display image generation unit 25.

Although the acoustic wave processing device, the signal processing method, and the program of the invention have been described in detail, the invention is not limited to the above-described example, and various improvements or alterations may be of course made without departing from the spirit of the invention.

For example, the element data storage unit 20 which stores element data for one image may not be provided, and transmission and reception of an ultrasonic wave may be performed a necessary number of times every time corresponding to one piece of element of interest in order to perform the multiline processing.

EXPLANATION OF REFERENCES

10, 110: ultrasound diagnostic apparatus
12: (ultrasound) probe
14: transmission unit
16: reception unit
18: A/D conversion unit
20: element data storage unit
21: region setting unit
22: Doppler processing unit
24: B mode processing unit
25: display image generation unit
26: display control unit
28: display unit
30: control unit
32: operating unit
34: storage unit
35: element data processing unit
36: transducer array
37, 116: image generation unit
38, 118: phasing addition unit
40: detection processing unit
42: DSC
44: image processing unit
46: image memory
47: processing region setting unit
48: delay time calculation unit
49, 120: superimposition processing unit
52: element
54: reflection point
56, 64: ultrasound beam
58: focal point
60: reception path
61: transmission path
62: element data
66: true element data
68: element data of ghost
114: data processing unit

What is claimed is:
1. An acoustic wave processing device comprising:
a probe which has an array of elements arranged to transmit acoustic beams, to receive acoustic echoes reflected from an inspection object, and to output analog element signals according to the received acoustic echoes, and
a processor,
wherein the processor is configured to:
perform A/D conversion on the analog element signals to generate first data as a digital signal,
select at least two pieces of data from the first data, each of the at least two pieces of data respectively generated by a transmission and reception of at least two acoustic beams, the at least two acoustic beams being sequential in time,
wherein each of the at least two acoustic beams is generated by a plurality of elements of the array, the plurality of elements defining a region and having a central element,
wherein the at least two acoustic beams have different central elements and regions that overlap each other,
wherein each of the at least two pieces of data has a transmission time between the transmission and reception of a respective one of the at least two acoustic beams, and one of the at least two pieces of data has a minimum transmission time,
perform superimposition processing on the at least two pieces of data to generate second data, the superimposition processing including calculation processing of a delay time according to a difference in the transmission time and the minimum transmission time due to a positional difference of the central elements and a correction processing on the each of the at least two pieces of data using the delay time,
generate a B mode image based on the second data,
generate a bloodstream image based on bloodstream information included in the first data,
set a bloodstream image region where the processor generates the bloodstream image,
set a processing region where the superimposition processing is performed based on information relating to the bloodstream image region,
generate a synthesized image of the B mode image and the bloodstream image based on the information relating to the bloodstream image region, and perform the superimposition processing only on the at least two pieces of data selected from the first data corresponding to one or more lines in the processing region,
wherein the processor is further configured to set the bloodstream image region based on an input from an operating unit, and
wherein the superimposition processing is not performed while the setting of the bloodstream image region by the operating unit is performed.

2. The acoustic wave processing device according to claim 1, wherein the processor further configured to calculate the bloodstream information based on a Doppler effect.

3. The acoustic wave processing device according to claim 1, wherein the information relating to the bloodstream image is at least one of the size, position, or shape of the processing region.

4. The acoustic wave processing device according to claim 2, wherein the information relating to the bloodstream image is at least one of the size, position, or shape of the processing region.

5. The acoustic wave processing device according to claim 1, wherein the processor is further configured to set the processing region to include the one or more lines passing through the bloodstream image region.

6. The acoustic wave processing device according to claim 1, wherein the processor is further configured to set the processing region to include the one or more lines passing through the bloodstream image region.

7. The acoustic wave processing device according to claim 1, wherein the processor is further configured to set the processing region to include the one or more lines passing through the bloodstream image region.

8. The acoustic wave processing device according to claim 1, wherein the processor is further configured to set the processing region to include one or more lines passing through the bloodstream image region.

9. A signal processing method for the acoustic wave processing device according to claim 1, which inspects an inspection object using a probe having an array of elements arranged to transmit acoustic beam, to receive acoustic echoes reflected from the inspection object, and to output analog element signals according to the received acoustic echoes, the signal processing method comprising:
performing A/D conversion on the analog element signals to generate first data as a digital signal;
selecting at least two pieces of data from the first data output in the A/D conversion step, each of the at least two pieces of data respectively generated by a transmission and reception of the at least two acoustic beams, the at least two acoustic beams being sequential in time,
wherein each of the at least two acoustic beams is generated by a plurality of elements of the array, the plurality of elements defining a region and having a central element,
wherein the at least two acoustic beams have different central elements and regions that overlap each other,
wherein each of the at least two pieces of data has a transmission time between the transmission and reception of a respective one of the at least two acoustic beams, and one of the at least two pieces of data has a minimum transmission time,
performing superimposition processing on the at least two pieces of data to generate second data, the superimposition processing including calculation processing of a delay time according to a difference in the transmission time and the minimum transmission time due to a positional difference of the central elements and a correction processing on the each of the at least two pieces of data using the delay time;
generating a B mode image based on the second data;
generating a bloodstream image based on bloodstream information included in the first data;
setting a bloodstream image region where the bloodstream image is generated;
setting a processing region where the superimposition processing is performed based on information relating to the bloodstream image region; and
generating a synthesized image of the B mode image and the bloodstream image based on the information relating to the bloodstream image region.

10. A non-transitory computer readable recording medium storing a program which causes a computer to execute a signal processing method for the acoustic wave processing device according to claim 1, which inspects an inspection object using a probe having an array of elements arranged to transmit acoustic beams, to receive acoustic echoes reflected from the inspection object, and to output analog element signals according to the received acoustic echoes, the signal processing method comprising:
performing A/D conversion on the analog element signal to generate first data as a digital signal;
selecting at least two pieces of data from the first data, each of the at least two pieces of data respectively generated by a transmission and reception of at least two acoustic beams, the at least two acoustic beams being sequential in time,
wherein each of the at least two acoustic beams is generated by a plurality of elements of the array, the plurality of elements defining a region and having a central element,
wherein the at least two acoustic beams have different central elements and regions that overlap each other,
wherein each of the at least two pieces of data has a transmission time between the transmission and reception of a respective one of the at least two acoustic beams, and one of the at least two pieces of data has a minimum transmission time,
performing superimposition processing on the at least two pieces of data to generate second data, the superimposition processing including calculation processing of a delay time according to a difference in the transmission time and the minimum transmission time due to a positional difference of the central elements and a correction processing on the each of the at least two pieces of data using the delay time;
generating a B mode image based on the second data;
generating a bloodstream image based on bloodstream information included in the first data;
setting a bloodstream image region where the bloodstream image is generated;
setting a processing region where the superimposition processing is performed based on information relating to the bloodstream image region; and
generating a synthesized image of the B mode image and the bloodstream image based on the information relating to the bloodstream image region.

11. An acoustic wave processing device comprising:
a probe which has an array of elements arranged to transmit acoustic beams, to receive acoustic echoes reflected from an inspection object, and to output analog element signals according to the received acoustic echoes; and a processor, wherein the processor is configured to:

perform A/D conversion on the analog element signals to generate first data as a digital signal, perform phasing addition on the first data to generate first reception data, select at least two pieces of data from the first reception data, each of the at least two pieces of data respectively generated by a transmission and reception of at least two acoustic beams, the at least two acoustic beams being sequential in time, wherein each of the at least two acoustic beams is generated by a plurality of elements of the array, the plurality of elements defining a region and having a central element, wherein the at least two acoustic beams have different central elements and regions that overlap each other, wherein each of the at least two pieces of data has a transmission time between the transmission and reception of a respective one of the at least two acoustic beams, and one of the at least two pieces of data has a minimum transmission time, perform superimposition processing on the selected at least two pieces of data to generate second reception data, the superimposition processing including calculation processing of a delay time according to a difference in the transmission time and the minimum transmission time due to a positional difference of the central elements and a correction processing on the each of the at least two pieces of data using the delay time, generate a B mode image based on the second reception data, generate a bloodstream image based on bloodstream information included in the first reception data, set a bloodstream image region where the processor generates the bloodstream image, set a processing region where the superimposition processing is performed based on information relating to the bloodstream image region, generate a synthesized image of the B mode image and the bloodstream image based on the information relating to the bloodstream image region, and perform the superimposition processing only on the at least two pieces of data selected from the first reception data corresponding to a line in the processing region, wherein the processor is further configured to set the bloodstream image region based on an input from an operating unit, and wherein the superimposition processing is not performed while the setting of the bloodstream image region by the operating unit is performed.

12. The acoustic wave processing device according to claim 11, wherein the processor further configured to calculate the bloodstream information based on a Doppler effect.

13. The acoustic wave processing device according to claim 11, wherein the information relating to the bloodstream image is at least one of the size, position, or shape of the processing region.

14. The acoustic wave processing device according to claim 11, wherein the processor further is configured to set the processing region to include a line passing through the bloodstream image region.

15. A signal processing method for the acoustic wave processing device according to claim 11, which inspects an inspection object using a probe having an array of elements arranged to transmit acoustic beams, to receive acoustic echoes reflected from the inspection object, and to output analog element signals according to the received acoustic echoes, the signal processing method comprising:

performing A/D conversion on the analog element signals to generate first data as a digital signal;

performing phasing addition on the first data to generate first reception data;

selecting at least two pieces of data from the first reception data, each of the at least two pieces of data respectively generated by a transmission and reception of at least two acoustic beams, the at least two acoustic beams being sequential in time, wherein each of the at least two acoustic beams is generated by a plurality of elements of the array, the plurality of elements defining a region and having a central element, wherein the at least two acoustic beams have different central elements and regions that overlap each other, wherein each of the at least two pieces of data has a transmission time between the transmission and reception of a respective one of the at least two acoustic beams, and one of the at least two pieces of data has a minimum transmission time, performing superimposition processing on the selected at least two pieces of data to generate second reception data, the superimposition processing including calculation processing of a delay time according to a difference in the transmission time and the minimum transmission time due to a positional difference of the central elements and a correction processing on the each of the at least two pieces of data using the delay time;

generating a B mode image based on or the second reception data;

generating a bloodstream image based on bloodstream information included in the first data;

setting a bloodstream image region where the bloodstream image is generated;

setting a processing region where the superimposition processing is performed based on information relating to the bloodstream image region; and generating a synthesized image of the B mode image and the bloodstream image based on the information relating to the bloodstream image region.

16. A non-transitory computer readable recording medium storing a program which causes a computer to execute a signal processing method for the acoustic wave processing device according to claim 11, which inspects an inspection object using a probe having an array of elements arranged to transmit acoustic beams, to receive acoustic echoes reflected from the inspection object, and to output analog element signals according to the received acoustic echoes, the signal processing method comprising:

performing A/D conversion on the analog element signals to generate first data as a digital signal;

performing phasing addition on the first data to generate first reception data;

selecting at least two pieces of data from the first reception data, each of the at least two pieces of data respectively generated by a transmission and reception of at least two acoustic beams, the at least two acoustic beams being sequential in time;

wherein each of the at least two acoustic beams is generated by a plurality of elements of the array, the plurality of elements defining a region and having a central element, wherein the at least two acoustic beams have different central elements and regions that overlap each other, wherein each of the at least two pieces of data has a transmission time between the transmission and reception of a respective one of the at least two acoustic beams, and one of the at least two pieces of data has a minimum transmission time, performing superimposition processing on the selected at least two pieces of data to generate second reception data, the superimposition processing including calculation processing of a delay time according to a difference in the transmission time and the minimum transmission time due to a positional difference of the central elements and a correction processing on the each of the at least two pieces of data using the delay time;

generating a B mode image based on the second reception data;

generating a bloodstream image based on bloodstream information included in the first data;

setting a bloodstream image region where the bloodstream image is generated;

setting a processing region where the superimposition processing is performed based on information relating to the bloodstream image region; and generating a synthesized image of the B mode image and the bloodstream image based on the information relating to the bloodstream image region.

* * * * *